(12) United States Patent
Whitby

(10) Patent No.: US 7,019,158 B1
(45) Date of Patent: Mar. 28, 2006

(54) CHIRAL ORGANOMETALLIC COMPOUNDS FOR USE IN ASYMMETRIC SYNTHESIS

(75) Inventor: Richard John Whitby, Hants (GB)

(73) Assignee: Avecia Limited, Manchester (GB)

( * ) Notice: Subject to any disclaimer, the term of this patent is extended or adjusted under 35 U.S.C. 154(b) by 170 days.

(21) Appl. No.: 10/485,315

(22) PCT Filed: Aug. 2, 2002

(86) PCT No.: PCT/GB02/03566

§ 371 (c)(1),
(2), (4) Date: Jan. 29, 2004

(87) PCT Pub. No.: WO03/013724

PCT Pub. Date: Feb. 20, 2003

(30) Foreign Application Priority Data

Aug. 3, 2001 (GB) .................................... 0119009

(51) Int. Cl.
*C07F 17/00* (2006.01)
*B01J 31/00* (2006.01)

(52) U.S. Cl. .......................... 556/136; 556/11; 556/12; 556/19; 556/22; 556/23; 556/46; 556/58; 556/137; 556/140; 502/152; 502/155

(58) Field of Classification Search .................. 556/11, 556/12, 19, 22, 23, 46, 58, 136, 137, 140; 502/152, 155
See application file for complete search history.

(56) References Cited

FOREIGN PATENT DOCUMENTS

| DE | 19630580 A1 | 2/1998 |
|----|----|----|
| EP | 0854147 A2 | 7/1998 |
| WO | WO 98/04570 | 2/1998 |
| WO | WO 99/28358 | 6/1999 |
| WO | WO 01/02323 A1 | 1/2001 |

OTHER PUBLICATIONS

Bitterwolf et al., Journal of Organometallic Chemistry, vol. 583, No. 1-2, pp. 152-161 (1999).*
Ciruelos, et al., Organometallics, 19:2240-2242 (2000).

* cited by examiner

*Primary Examiner*—Porfirio Nazario-Gonzalez
(74) *Attorney, Agent, or Firm*—Morgan, Lewis & Bockuis LLP

(57) ABSTRACT

Chiral organometallic compounds are provided which comprise certain non-symmetrically substituted cyclopentadiene complexed to a transition metal. The cyclopentadiene has a second coordinating group which also complexes the transition metal and is attached to the cyclopentadiene by means of a chiral connecting chain. Preferred transition metals include rhodium, ruthenium, iridium, cobalt, iron, manganese, chromium, tungsten, molybdenum, nickel, palladium, or platinum. These chiral organometallic compounds find use in asymmetric synthesis to produce chiral compounds.

15 Claims, No Drawings

CHIRAL ORGANOMETALLIC COMPOUNDS FOR USE IN ASYMMETRIC SYNTHESIS

The present invention relates to organometallic, chiral compounds, to processes for preparing said compounds and to methods of using said compounds in asymmetric synthesis to produce chiral products.

There is a need for stable organometallic chiral compounds for use in asymmetric synthesis of chiral products which can be readily synthesised from intermediates.

We have found that certain non-symmetrically substituted cyclopentadienes are predisposed to form chiral complexes with transition metals and that by incorporating a second coordinating group on a chiral connecting chain, provides a second control element for enatioinduction reaction and improves the stability of the complex towards dissociation.

According to a first aspect of the present invention there is provided compounds of formula (1):

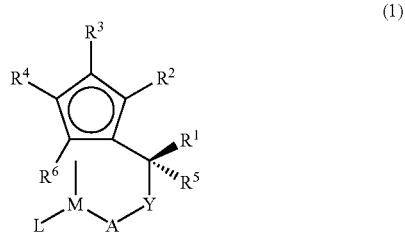

wherein

L is optionally one or more groups which are removable during a chemical reaction;

M is a transition metal selected from Groups 6, 7, 8, 9 and 10;

Y is an optionally substituted linking group;

A is an optionally substituted heteroatom capable of bonding or coordinating to metal (M); and

EITHER:

(a) $R^5$ and $R^6$ are hydrogen;

$R^1$ is optionally substituted hydrocarbyl, optionally substituted heterocyclyl, or tri-hydrocarbylsilyl, or $R^1$ & Y are linked in such a way as to form an asymmetrically substituted ring, or $R^1$ & A are linked in such a way as to form an optionally substituted heterocyclic ring;

$R^2$ is optionally substituted hydrocarbyl, optionally substituted heterocyclyl, or tri-hydrocarbylsilyl;

$R^3$ and $R^4$ are independently optionally substituted hydrocarbyl, optionally substituted heterocyclyl, tri-hydrocarbylsilyl or hydrogen; or one or more of $R^2$ & $R^3$ and $R^3$ & $R^4$ are linked in such a way as to form an optionally substituted ring optionally comprising one or more heteroatoms; provided that $R^2$, $R^3$, and $R^4$ are selected such that the cyclopentadiene ring to which they are attached is asymmetrically substituted;

OR:

(b) $R^3$ is hydrogen, optionally substituted hydrocarbyl, optionally substituted heterocyclyl, or tri-hydrocarbylsilyl; and either (i) $R^5$ & $R^2$ are linked in such a way as to form an optionally substituted non-aromatic ring system optionally comprising one or more heteroatoms; and $R^1$, $R^4$ and $R^6$ are independently hydrogen, optionally substituted hydrocarbyl, optionally substituted heterocyclyl, or tri-hydrocarbylsilyl; or $R^4$ & $R^6$ are linked in such a way as to form an optionally substituted non-aromatic ring system optionally comprising one or more heteroatoms and $R^4$ is hydrogen, optionally substituted hydrocarbyl, optionally substituted heterocyclyl, or tri-hydrocarbylsilyl; or $R^4$ & $R^6$ are linked in such a way as to form an optionally substituted ring optionally comprising one or more heteroatoms and $R^1$ is hydrogen, optionally substituted hydrocarbyl, optionally substituted heterocyclyl, or tri-hydrocarbylsilyl; or (ii) $R^5$, $R^1$ & $R^2$ are linked in such a way as to form an optionally substituted non-aromatic asymmetric ring system optionally comprising one or more heteroatoms; and $R^4$ and $R^6$ are idependently hydrogen, optionally substituted hydrocarbyl, optionally substituted heterocyclyl, or tri-hydrocarbylsilyl; or $R^4$ & $R^6$ are linked in such a way as to form an optionally substituted ring optionally comprising one or more heteroatoms.

The present invention provides a chiral, organometallic compound which, at a molecular level comprises a carbon to carbon bond joining a chiral carbon atom to both a carbon atom of a cyclopentadienyl ring (attached to a metal atom) that is non-symmetrically substituted and to a group which also coordinates to the metal centre.

By having a cyclopentadienyl ring that is not symmetrically substituted the organometallic compound possesses planar chirality and by having a chiral group attached to the non-symmetrically substituted cyclopentadiene ring the faces of the cyclopentadiene are diastereotopic so that metallation is directed predominantly to one face. The complexes generated by metallation of the alternate faces of the non-symmetrically substituted cyclopentadienyl ring are diastereotopic and may thus be separated. Also, once complexed to the metal of the organometallic compound, the non-symmetrically substituted cydopentadiene ring, and the chiral connecting chain, provide two control elements for enantioinduction in reactions.

By including a second group to coordinate to the metal the orientation of the cyclopentadiene is fixed, and stability towards dissociation from the metal of both groups is improved.

Hydrocarbyl groups which may be represented by $R^{1-6}$ independently include alkyl, alkenyl and aryl groups, and any combination thereof, such as aralkyl and alkaryl, for example benzyl groups.

Alkyl groups which may be represented by $R^{1-6}$ include linear and branched alkyl groups comprising up to 20 carbon atoms, particularly from 1 to 10 carbon atoms and preferably from 1 to 6 carbon atoms, for example 1 to 4 carbon atoms. When the alkyl groups are branched, the groups often comprising up to 10 branch chain carbon atoms, preferably up to 4 branch chain atoms. In certain embodiments, the alkyl group may be cyclic, commonly comprising from 3 to 10 carbon atoms, preferably 3 to 8 and especially 3 to 6 carbon atoms in the largest ring and optionally featuring one or more bridging rings. Examples of alkyl groups which may be represented by $R^{1-6}$ include methyl, ethyl, propyl, 2-propyl, butyl, 2-butyl, t-butyl, n-hexyl, cyclopropyl, cyclopentyl and cyclohexyl groups.

Alkenyl groups which may be represented by $R^{1-6}$ include $C_{2-20}$, and preferably $C_{2-6}$ alkenyl groups. One or more carbon—carbon double bonds may be present. The alkenyl group may carry one or more substituents, particularly phenyl substituents. When the alkenyl groups are branched, the groups often comprising up to 10 branch chain carbon atoms, preferably up to 4 branch chain atoms. In certain embodiments, the alkenyl group may be cyclic, commonly comprising from 3 to 10 carbon atoms, preferably 3 to 8 and especially 3 to 6 carbon atoms in the largest ring and optionally featuring one or more bridging rings. Examples of alkenyl groups include vinyl, styryl, cyclohexenyl and indenyl groups.

Aryl groups which may be represented by $R^{1-6}$ may contain 1 ring or 2 or more fused rings which may include cycloalkyl, aryl or heterocyclic rings. Preferably aryl groups are optionally substituted phenyl or napthyl groups, more preferably phenyl groups. Examples of aryl groups which may be represented by $R^{1-6}$ include phenyl, tolyl, fluorophenyl, chlorophenyl, bromophenyl, trifluoromethylphenyl, anisyl, naphthyl and ferrocenyl groups.

Heterocyclic groups which may be represented by $R^{1-6}$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. Examples of heterocyclic groups which may be represented by $R^{1-6}$ include piperidinyl, morpholinyl, pyrrolidinyl, pyridyl, pyrimidyl, pyrrolyl, thiophenyl, furanyl, indolyl, quinolyl, isoquinolyl, imidazoyl and triazoyl groups.

Trihydrocarbylsilyl groups which may be represented by $R^{1-6}$ independently include silyl groups wherein the hydrocarbyl groups may be the same or different and are as defined for $R^1$ above. Preferred trihydrocarbylsilyl groups include trialklylsilyl, dialkylarylsilyl, alkyldiarylsilyl and triarylsilyl groups, and more preferably wherein alkyl is a $C_{1-8}$alkyl group and aryl is a phenyl group. Examples of trihydrocarbylsilyl groups include $(CH_3)_3Si$, $(CH_3)_2PhS_1$, $CH_3(Ph)_2Si$ and $(Ph)_3Si$.

When any of $R^{1-6}$ is a substituted hydrocarbyl or heterocyclic group, the substituent(s) should be such so as not to adversely affect the rate or stereoselectivety of the reaction. Optional substituents include halogen, cyano, nitro, hydroxy, amino, thiol, acyl, hydrocarbyl, perhalogentated hydrocarbyl, heterocyclyl, hydrocarbyloxy, mono or dihydrocarbylamino, hydrocarbylamino, trihydrocarbylsilyl, esters, carbonates, amides, sulphonyl and sulphonamido groups wherein the hydrocarbyl and heterocyclyl groups are as defined for $R^1$ above, and wherein perhalogenated hydrocarbyl groups include perhalogenated alkyl groups, for example $—CF_3$ and $—C_2F_5$, and perhalogenated aryl groups, and any combination thereof, such as perhalogenated aralkyl and alkaryl groups. One or more substituents may be present.

Optionally substituted linking groups which may be represented by Y include optionally bridges of from 1 to 6 atoms preferably in which at least one atom is carbon and optionally at least one atom is any of N, O, S, Si or P. Preferred linking groups include optionally substituted $C_{1-5}$alkylene bridges, optionally substituted alkylenearyl bridges, and optionally substituted heteroatom containing bridges, for example optionally substituted silyl and alkylenesilyl bridges. Examples of linking groups include $—CH_2—$, $—(CH_2)_2—$, $—(CH_2)_3—$, $—(CH_2)_4—$, $—(CH_2)_5—$, $—CH_2SiMe_2—$, and $—CH_2SiMe_2CH_2—$.

Optionally substituted atoms capable of bonding or coordinating to metal (M) which may be represented by A include optionally substituted O, P, N or S atoms. When A is an optionally substituted O, P, N or S atom, the O, P, N or S atom may be substituted by groups selected from those groups defined above for $R^1$. Examples of optionally substituted atoms capable of bonding or coordinating to metal (M) include $PPh_2$, $PCy_2$, $PMe_2$, $SPh$, $SMe$, $S$, $NPh_2$, $NMe_2$, $NPh$, $NMe$, $NTs$, $OMe$ and $O$. (where Cy=Cyclohexyl).

Groups which are removable during a chemical reaction which are represented by L include halides, for example fluoride, chloride, bromide and iodide, hydrocarbyloxy groups, siloxy groups, hydrocarbyl groups, phosphines, ethers, thioethers, carbon monoxide, hydrocarbylisocynates, and $η^2$-alkenes, $η^2$-cycloalkenes and $η^2$-alkynes for example $η^2$-ethene, $η^2$-cyclooctene and $η^2$-diphenylacetylene.

Transition metal selected from Groups 6, 7, 8, 9 and 10 which are represented by M include rhodium, ruthenium, iridium, cobalt, iron, manganese, chromium, tungsten, molybdenum, nickel, palladium, or platinum, and are preferably rhodium, iridium or ruthenium.

Rings which may be represented by $R^1$ & Y, $R^1$ & A, $R^2$ & $R^3$, $R^3$ & $R^4$, $R^1$ & $R^6$, $R^4$ & $R^6$, $R^2$ & $R^5$ or by $R^1$, $R^2$ & $R^5$ commonly comprise from 3 to 10 ring atoms, preferably 3 to 8 and especially 5 or 6 ring atoms. Optionally they may be fused ring systems or may feature one or more bridging rings. Preferably in rings represented by $R^3$ & $R^4$, $R^1$ & $R^6$, $R^4$ & $R^6$, $R^2$ & $R^5$ or by $R^1$, $R^2$ & $R^5$ the ring atoms which are not derived from the cyclopentadienyl ring to which M is bonded are preferably saturated.

In a preferred aspect of the present invention there is provided a compound of formula (1):

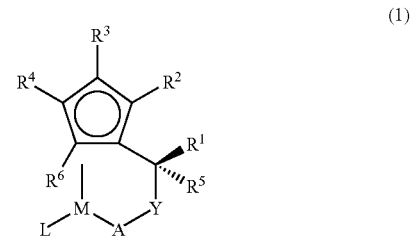

(1)

wherein:
  L is, independently, one or more groups which are removable during a chemical reaction;
  M is rhodium, ruthenium, iridium, cobalt, iron, manganese, chromium, tungsten, molybdenum, nickel, palladium, or platinum;
  Y is a linking chain comprising an optionally substituted $C_{1-5}$alkyl or alkylaryl, or optionally substituted silyl bridge, or optionally substituted heteroatom containing bridge;
  A is an atom (which may carry substituents) which may bond to the metal, preferably $PR^8R^9$, $NR^8$, $NR^8R^9$, O, $OR^8$, S or $SR^8$ wherein $R^8$ and $R^9$ may be independently hydrogen, alkyl, aryl, arylalkyl, aryloxyalkyl, alkoxyalkyl, alkoxyalkoxyalkyl, cycloalkyl, cycloalkylalkyl, heteroaryl, heteroarylalkyl, heteroaryloxyalkyl, trialkylsilyl, dialkylarylsilyl, alkyldiarylsilyl, triarylsilyl, acyl, arylsulphonate, alkylsulphonate; and
  EITHER:
  (a) $R^5$ and $R^6$ are hydrogen;
  $R^1$ and $R^2$ are trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^2$ is as above and $R^1$ joins to Y to form an asymmetrically substituted $C_{3-8}$ cycloalkyl, $C_{3-8}$ cycloalkenyl or $C_{3-8}$ heterocyclyl ring optionally substituted with hydroxy, trialkylsilyl, alkyl, alkoxy, aryl, arylalkyl, aryloxyallyl, alkoxyalkyl, alkoxyalkoxyalkyl, cycloalky, cycloalkylalkyl, heteroaryl, heteroarylalkyl or heteroaryloxyalkyl; or $R^2$ is as above and $R^1$ joins to A to form an optionally substituted heterocyclic ring; $R^3$ and $R^4$ are the same or different and are selected from the substituents already recited for $R^1$ and $R^2$ and may also be, independently, hydrogen; or, one or more of $R^2$ and $R^3$, $R^3$ and $R^4$ join to form an optionally substituted ring optionally comprising one or more heteroatoms OR:

(b) $R^3$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; and either (i) $R^5$ and $R^2$ join to form an optionally substituted non-aromatic ring system optionally comprising one or more heteroatoms; and $R^1$, $R^4$ and $R^6$ are independently hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ & $R^6$ join to form an optionally substituted non-aromatic ring system optionally comprising one or more heteroatoms and $R^4$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^4$ & $R^6$ join to form an optionally substituted ring system optionally comprising one or more heteroatoms and $R^1$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or (ii) $R^5$, $R^1$ and $R^2$ are linked in such a way as to form an optionally substituted non-aromatic asymmetric ring system comprising one or more heteroatoms; and $R^4$ and $R^6$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^4$ & $R^6$ join to form an optionally substituted ring system optionally comprising one or more heteroatoms.

In this preferred aspect of the present invention, cycloalkyl and cycloalkenyl rings preferably are optionally substituted by hydroxy, alkoxy, alkyl, aryl or arylalkyl groups; arylalkyl groups are preferably phenyl$(C_{1-4})$alkyl, for example, benzyl, 1-phenyleth-1-yl, 2-phenyleth-1-yl, 2-phenylprop-2-yl, 1-phenylprop-2-yl or 1-phenyl-2-methylprop-2-yl; aryloxyalkyl groups are preferably phenoxy $(C_{1-4})$alkyl, for example, phenoxymethyl or 1- or 2-phenoxyethyl; alkoxyalkyl and alkoxyalkoxyalkyl groups are preferably $C_{1-6}$alkoxy$(C_{1-6})$alkyl and $C_{1-6}$alkoxy$(C_{1-6})$alkoxy$(C_{1-6})$alkyl respectively, for example, methoxymethyl, ethoxymethyl or methoxy(ethoxymethyl); cycloalkylalkyl groups are preferably $C_{3-8}$ cycloalkyl$(C_{1-4})$alkyl, for example, cyclopropylmethyl, cyclohexylmethyl or cyclohexylethyl; heterocyclyl rings are not aromatic and preferably contain from 3 to 8, especially from 3 to 6, atoms selected from the group comprising carbon, oxygen, nitrogen or silicon, preferably heterocyclyl rings contain 1, 2 or 3 heteroatoms, for example piperidine, morpholine or pyrrolidine, and are preferably, optionally substituted by hydroxy, alkoxy, alkyl, aryl or arylalkyl groups; heteroaryl includes aromatic 5 or 6 membered rings comprising one or more (preferably 1, 2 or 3) heteroatoms (preferably nitrogen, oxygen or sulphur), for example, pyridine, pyrimidine, triazine (1,2,3-, 1,2,4- or 1,3,5-), pyrrole, quinoline or isoquinoline; heteroarylalkyl is preferably heteroaryl$(C_{1-4})$alkyl, for example pyrid-2-ylmethyl or pyrid-2-ylmethyl; heteroaryloxyalkyl is preferably heteroaryloxy$(C_{1-14})$alkyl, for example, pyrid-2-yloxymethyl or pyrid-4-yloxymethyl.

In this preferred aspect of the present invention when any aryl and heteroaryl groups are optionally substituted by one or more substituents, preferred substituents are halogen, hydroxy, mercapto, $C_{1-8}$alkyl (especially methyl or ethyl), $C_{1-8}$alkoxy (especially methoxy), $C_{1-4}$alkylthio (especially methylthio), hydroxy$(C_{1-4})$alkyl, $C_{1-4}$alkoxy$(C_{1-4})$alkyl, $C_{3-6}$cycloalkyl, $C_{3-6}$cycloalkyl$(C_{1-4})$alkyl, optionally substituted methylenedioxy or ethylenedioxy (for example optionally substituted by alkyl) or —NR'R", in which R' and R" are independently hydrogen, $C_{1-4}$alkyl, $C_{3-6}$cycloalkyl, $C_{3-6}$cycloalkyl$(C_{1-4})$alkyl, phenyl or benzyl, the phenyl and benzyl groups being optionally substituted with $C_{1-4}$alkyl or $C_{1-4}$alkoxy.

Preferably in compounds of formula (1), $R_5$ and $R^6$ are hydrogen.

Preferably in compounds of formula (1) Y is an optionally substituted $C_{1-4}$ alkyl chain.

Preferably in compounds of formula (1) A is $PR^8R^9$ where $R^8$ and $R^9$ are independently aryl (preferably phenyl) or alkyl (including cycloalkyl).

Preferably in compounds of formula (1) L is carbon monoxide, halide (especially chloride), $\eta^2$-ethene or phosphines (especially $PPh_3$).

In further preferred aspect of the present invention there is provided a compound of Formula (2) or (3):

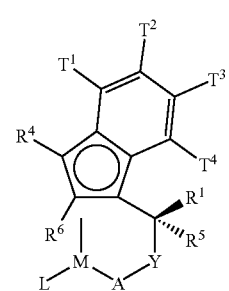

(2)

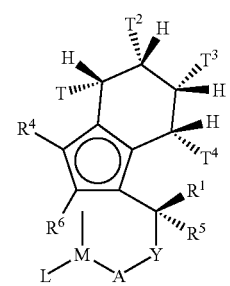

(3)

wherein:
  L are independently one or more groups which are removable during a chemical reaction;
  M is rhodium, ruthenium, iridium, cobalt, iron, manganese, chromium, tungsten, molybdenum, nickel, palladium, or platinum;
  Y is a linking chain comprising an optionally substituted $C_{1-5}$alkyl or alkylaryl, or optionally substituted silyl bridge, or optionally substituted hetereoatom containing bridge;
  A is an atom (which may carry substituents) which may bond to the metal, preferably $PR^8R^9$, $NR^8$, $NR^8R^9$, $SR^8$;
  $R^1$ is trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ joins to Y to form an asymmetrically substituted $C_{3-8}$cycloalkyl, $C_{3-8}$cycloalkenyl or $C_{3-8}$heterocyclyl ring optionally substituted with hydroxy, trialkylsilyl, alkyl, alkoxy, aryl, arylalkyl, aryloxyallyl, alkoxyalkyl, alkoxyalkoxyalkyl, cycloalky, cycloalkylalkyl, heteroaryl, heteroarylalkyl or heteroaryloxyalkyl; or $R^1$ joins to A to form an optionally substituted heterocyclic ring;
  $R^4$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl;
  $R^5$ and $R^6$ are hydrogen; and
  $T^1$, $T^2$, $T^3$, $T^4$ are the same or different and are hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl.

Preferably in this aspect of the present invention Y in formula (2) or (3) is an optionally substituted $C_{1-4}$alkyl chain.

Preferably in this aspect of the present invention A in formula (2) or (3) is $PR^8R^9$ where $R^8$ and $R^9$ are independently aryl (preferably phenyl) or alkyl (including cycloalkyl).

In yet a further preferred aspect of the present invention there is provided a compound of formula (4):

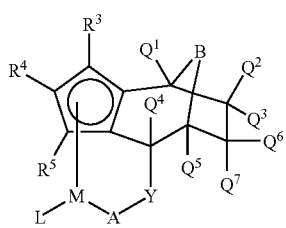

(4)

wherein:
  L is independently one or more groups which are removable during a chemical reaction;
  M is rhodium, ruthenium, iridium, cobalt, iron, manganese, chromium, tungsten, molybdenum, nickel, palladium, or platinum;
  Y is a linking chain comprising an optionally substituted $C_{1-5}$alkyl or alkylaryl, or optionally substituted silyl bridge, or optionally substituted hetereoatom containing bridge;
  A is an atom (which may carry substituents) which may bond to the metal, preferably $PR^8R^9$, $NR^8$, $NR^8R^9$, $SR^8$;
  B is a bridge comprising an optionally substituted $C_{1-3}$alkyl bridge or an optionally substituted 1–3 atom bridge wherein at least one atom is a heteroatom and any remaining atoms are carbon atoms, preferably wherein any heteroatoms are selected from the group comprising N, O, P, S and Si;
  Y is an optionally substituted $C_{1-3}$alkyl bridge; and
  $R^3$, $R^4$, $R^6$, $R^8$, $R^9$, $Q^1$, $Q^2$, $Q^3$, $Q^4$, $Q^5$, $Q^6$, $Q^7$ are the same or different and are hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or
  $R^4$ & $R^6$ are linked in such a way as to form an optionally substituted ring optionally comprising one or more heteroatoms; or
  $Q^4$ & $R^6$ are linked in such a way as to form an optionally substituted non-aromatic ring system comprising one or more heteratoms; and additionally
  $Q^2$ and $Q^3$ may also be alkoxy, aryloxy or silyloxy; or $Q^2$ and $Q^3$ combine to form a carbonyl, imine, or alkylidene group.

In yet a further preferred aspect of the present invention there is provided a compound of formula (5):

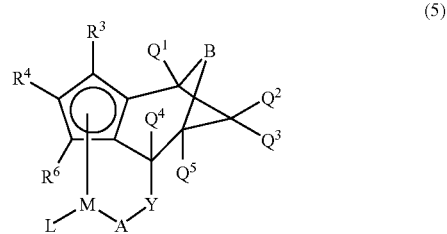

(5)

wherein:
  L is independently one or more groups which are removable during a chemical reaction;
  M is rhodium, ruthenium, iridium, cobalt, iron, manganese, chromium, tungsten, molybdenum, nickel, palladium, or platinum;
  Y is a linking chain comprising an optionally substituted $C_{1-5}$alkyl or alkylaryl, or optionally substituted silyl bridge, or optionally substituted hetereoatom containing bridge;
  A is an atom (which may carry substituents) which may bond to the metal, preferably $PR^8R^9$, $NR^8$, $NR^8R^9$, $SR^8$;
  B is a bridge comprising an optionally substituted $C_{1-3}$alkyl bridge or an optionally substituted 1–3 atom bridge wherein at least one atom is a heteroatom and any remaining atoms are carbon atoms, preferably wherein any heteroatoms are selected from the group comprising N, O, P, S and Si;
  Y is an optionally substituted $C_{1-3}$alkyl bridge; and
  $R^3$, $R^4$, $R^6$, $R^8$, $R^9$, $Q^1$, $Q^2$, $Q^3$, $Q^4$, $Q^5$, $Q^6$, $Q^7$ are the same or different and are hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^4$ & $R^6$ are linked in such a way as to form an optionally substituted ring optionally comprising one or more heteroatoms; or $Q^4$ & $R^6$ are linked in such a way as to form an optionally substituted non-aromatic ring system comprising one or more heteratoms; and additionally $Q^2$ and $Q^3$ may also be alkoxy, aryloxy or silyloxy; or $Q^2$ and $Q^3$ combine to form a carbonyl, imine, or alkylidene group.

Preferably in compounds of formula (4) and (5), Y is an optionally substituted $C_{1-4}$ alkyl, or aryl, or alkylaryl chain.

Preferably in compounds of formula (4) and (5), A is $PR^8R^9$ where $R^8$ and $R^9$ are independently aryl (preferably phenyl) or alkyl (including cycloalkyl).

Preferably in compounds of formula (4) and (5), M is rhodium, iridium, or ruthenium.

The compounds in the following Tables are preferred.

TABLE 1

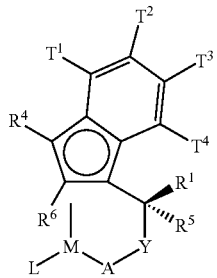

(2)

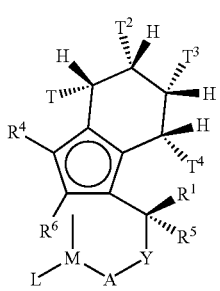

(3)

| Formula | A | Y | $R^1$ | $R^4$ | $R^5$ | $R^6$ | $T^1$ | $T^2$ | $T^3$ | $T^4$ |
|---|---|---|---|---|---|---|---|---|---|---|
| (2), (3) | $PPh_2$ | $(CH_2)_n$ | Me | H | H | H | H | H | H | H |
| (2), (3) | $PPh_2$ | $(CH_2)_n$ | Ph | H | H | H | H | H | H | H |
| (2), (3) | $PPh_2$ | $(CH_2)_n$ | Cy | H | H | H | H | H | H | H |
| (2), (3) | $PPh_2$ | $(CH_2)_n$ | t-Bu | H | H | H | H | H | H | H |
| (2), (3) | $PPh_2$ | $(CH_2)_n$ | Me | $SiMe_3$ | H | H | H | H | H | H |
| (2), (3) | $PPh_2$ | $(CH_2)_n$ | Ph | $SiMe_3$ | H | H | H | H | H | H |
| (2), (3) | $PPh_2$ | $(CH_2)_n$ | Cy | $SiMe_3$ | H | H | H | H | H | H |
| (2), (3) | $PPh_2$ | $(CH_2)_n$ | t-Bu | $SiMe_3$ | H | H | H | H | H | H |
| (2), (3) | $PPh_2$ | $(CH_2)_n$ | Me | t-Bu | H | H | H | H | H | H |

TABLE 1-continued

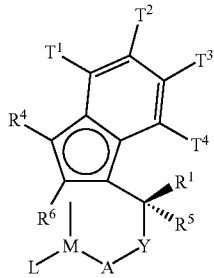

(2)

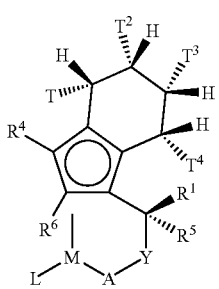

(3)

| Formula | A | Y | $R^1$ | $R^4$ | $R^5$ | $R^6$ | $T^1$ | $T^2$ | $T^3$ | $T^4$ |
|---|---|---|---|---|---|---|---|---|---|---|
| (2), (3) | $PPh_2$ | $(CH_2)_n$ | Ph | t-Bu | H | H | H | H | H | H |
| (2), (3) | $PPh_2$ | $(CH_2)_n$ | Cy | t-Bu | H | H | H | H | H | H |
| (2), (3) | $PPh_2$ | $(CH_2)_n$ | t-Bu | t-Bu | H | H | H | H | H | H |
| (2), (3) | $PPh_2$ | $(CH_2)_n$ | Me | Ph | H | H | H | H | H | H |
| (2), (3) | $PPh_2$ | $(CH_2)_n$ | Ph | Ph | H | H | H | H | H | H |
| (2), (3) | $PPh_2$ | $(CH_2)_n$ | Cy | Ph | H | H | H | H | H | H |
| (2), (3) | $PPh_2$ | $(CH_2)_n$ | t-Bu | Ph | H | H | H | H | H | H |
| (2), (3) | $PPh_2$ | $(CH_2)_n$ | Me | Cy | H | H | H | H | H | H |
| (2), (3) | $PPh_2$ | $(CH_2)_n$ | Ph | Cy | H | H | H | H | H | H |
| (2), (3) | $PPh_2$ | $(CH_2)_n$ | Cy | Cy | H | H | H | H | H | H |
| (2), (3) | $PPh_2$ | $(CH_2)_n$ | t-Bu | Cy | H | H | H | H | H | H |
| (2), (3) | $PPh_2$ | $(CH_2)_n$ | Me | H | H | H | Me | H | H | Me |
| (2), (3) | $PPh_2$ | $(CH_2)_n$ | Ph | H | H | H | Me | H | H | Me |
| (2), (3) | $PPh_2$ | $(CH_2)_n$ | Cy | H | H | H | Me | H | H | Me |
| (2), (3) | $PPh_2$ | $(CH_2)_n$ | t-Bu | H | H | H | Me | H | H | Me |
| (2), (3) | $PPh_2$ | $(CH_2)_n$ | Me | $SiMe_3$ | H | H | Me | H | H | Me |
| (2), (3) | $PPh_2$ | $(CH_2)_n$ | Ph | $SiMe_3$ | H | H | Me | H | H | Me |
| (2), (3) | $PPh_2$ | $(CH_2)_n$ | Cy | $SiMe_3$ | H | H | Me | H | H | Me |
| (2), (3) | $PPh_2$ | $(CH_2)_n$ | t-Bu | $SiMe_3$ | H | H | Me | H | H | Me |
| (2), (3) | $PPh_2$ | $(CH_2)_n$ | Me | t-Bu | H | H | Me | H | H | Me |
| (2), (3) | $PPh_2$ | $(CH_2)_n$ | Ph | t-Bu | H | H | Me | H | H | Me |
| (2), (3) | $PPh_2$ | $(CH_2)_n$ | Cy | t-Bu | H | H | Me | H | H | Me |
| (2), (3) | $PPh_2$ | $(CH_2)_n$ | t-Bu | t-Bu | H | H | Me | H | H | Me |
| (2), (3) | $PPh_2$ | $(CH_2)_n$ | Me | Ph | H | H | Me | H | H | Me |
| (2), (3) | $PPh_2$ | $(CH_2)_n$ | Ph | Ph | H | H | Me | H | H | Me |
| (2), (3) | $PPh_2$ | $(CH_2)_n$ | Cy | Ph | H | H | Me | H | H | Me |
| (2), (3) | $PPh_2$ | $(CH_2)_n$ | t-Bu | Ph | H | H | Me | H | H | Me |
| (2), (3) | $PPh_2$ | $(CH_2)_n$ | Me | Cy | H | H | Me | H | H | Me |
| (2), (3) | $PPh_2$ | $(CH_2)_n$ | Ph | Cy | H | H | Me | H | H | Me |
| (2), (3) | $PPh_2$ | $(CH_2)_n$ | Cy | Cy | H | H | Me | H | H | Me |
| (2), (3) | $PPh_2$ | $(CH_2)_n$ | t-Bu | Cy | H | H | Me | H | H | Me |

Where M—L = Rh(CO) or Ru($PPh_3$)Cl; and n = 1, 2 or 3
Cy = cyclohexyl

TABLE 2

(6), (7)

| Formula | A | $R^1$ | $R^{10}$ | $R^{11}$ |
|---|---|---|---|---|
| (6), (7) | $PPh_2$ | Ph | H | Ph |
| (6), (7) | $PPh_2$ | 1-Napthyl | H | 1-Napthyl |
| (6), (7) | $PPh_2$ | Cy | H | Ph |
| (6), (7) | $PPh_2$ | Cy | H | 1-Napthyl |
| (6), (7) | $PPh_2$ | Cy | Ph | H |
| (6), (7) | $PPh_2$ | Cy | 1-Napthyl | H |
| (6), (7) | $PPh_2$ | Me | H | Ph |
| (6), (7) | $PPh_2$ | Me | H | 1-Napthyl |
| (6), (7) | $PPh_2$ | Me | Ph | H |
| (6), (7) | $PPh_2$ | Me | 1-Napthyl | H |
| (6), (7) | $PPh_2$ | t-Bu | H | Ph |
| (6), (7) | $PPh_2$ | t-Bu | H | 1-Napthyl |
| (6), (7) | $PPh_2$ | t-Bu | Ph | H |
| (6), (7) | $PPh_2$ | t-Bu | 1-Napthyl | H |

Where M—L = Rh(CO) or Ru($PPh_3$)Cl; $R^{4-6}$ are each H, $T^{1-4}$ are each H
Cy = cyclohexyl

TABLE 3

(8), (9)

| Formula | A | Y | $Q^2$ | $Q^1$ | $Q^4$ | $R^6$ | $R^4$ |
|---|---|---|---|---|---|---|---|
| (8), (9) | $PPh_2$ | $(CH_2)_n$ | H | H | H | —$(CH_2)_4$— or are each H | |
| (8), (9) | $PPh_2$ | $(CH_2)_n$ | Me | H | H | —$(CH_2)_4$— or are each H | |
| (8), (9) | $PPh_2$ | $(CH_2)_n$ | Bu | H | H | —$(CH_2)_4$— or are each H | |
| (8), (9) | $PPh_2$ | $(CH_2)_n$ | Cy | H | H | —$(CH_2)_4$— or are each H | |
| (8), (9) | $PPh_2$ | $(CH_2)_n$ | i-Pr | H | H | —$(CH_2)_4$— or are each H | |
| (8), (9) | $PPh_2$ | $(CH_2)_n$ | Ph | H | H | —$(CH_2)_4$— or are each H | |
| (8), (9) | $PPh_2$ | $(CH_2)_n$ | H | Me | H | —$(CH_2)_4$— or are each H | |
| (8), (9) | $PPh_2$ | $(CH_2)_n$ | Me | Me | H | —$(CH_2)_4$— or are each H | |
| (8), (9) | $PPh_2$ | $(CH_2)_n$ | Bu | Me | H | —$(CH_2)_4$— or are each H | |
| (8), (9) | $PPh_2$ | $(CH_2)_n$ | Cy | Me | H | —$(CH_2)_4$— or are each H | |
| (8), (9) | $PPh_2$ | $(CH_2)_n$ | i-Pr | Me | H | —$(CH_2)_4$— or are each H | |
| (8), (9) | $PPh_2$ | $(CH_2)_n$ | Ph | Me | H | —$(CH_2)_4$— or are each H | |
| (8), (9) | $PPh_2$ | $(CH_2)_n$ | H | H | Me | —$(CH_2)_4$— or are each H | |
| (8), (9) | $PPh_2$ | $(CH_2)_n$ | Me | H | Me | —$(CH_2)_4$— or are each H | |
| (8), (9) | $PPh_2$ | $(CH_2)_n$ | Bu | H | Me | —$(CH_2)_4$— or are each H | |
| (8), (9) | $PPh_2$ | $(CH_2)_n$ | Cy | H | Me | —$(CH_2)_4$— or are each H | |
| (8), (9) | $PPh_2$ | $(CH_2)_n$ | i-Pr | H | Me | —$(CH_2)_4$— or are each H | |
| (8), (9) | $PPh_2$ | $(CH_2)_n$ | Ph | H | Me | —$(CH_2)_4$— or are each H | |
| (8), (9) | $PPh_2$ | $(CH_2)_n$ | H | Me | Me | —$(CH_2)_4$— or are each H | |
| (8), (9) | $PPh_2$ | $(CH_2)_n$ | Me | Me | Me | —$(CH_2)_4$— or are each H | |
| (8), (9) | $PPh_2$ | $(CH_2)_n$ | Bu | Me | Me | —$(CH_2)_4$— or are each H | |
| (8), (9) | $PPh_2$ | $(CH_2)_n$ | Cy | Me | Me | —$(CH_2)_4$— or are each H | |
| (8), (9) | $PPh_2$ | $(CH_2)_n$ | i-Pr | Me | Me | —$(CH_2)_4$— or are each H | |
| (8), (9) | $PPh_2$ | $(CH_2)_n$ | Ph | Me | Me | —$(CH_2)_4$— or are each H | |
| (8), (9) | $PPh_2$ | $(CH_2)_n$ | H | H | Ph | —$(CH_2)_4$— or are each H | |
| (8), (9) | $PPh_2$ | $(CH_2)_n$ | Me | H | Ph | —$(CH_2)_4$— or are each H | |
| (8), (9) | $PPh_2$ | $(CH_2)_n$ | Bu | H | Ph | —$(CH_2)_4$— or are each H | |
| (8), (9) | $PPh_2$ | $(CH_2)_n$ | Cy | H | Ph | —$(CH_2)_4$— or are each H | |
| (8), (9) | $PPh_2$ | $(CH_2)_n$ | i-Pr | H | Ph | —$(CH_2)_4$— or are each H | |
| (8), (9) | $PPh_2$ | $(CH_2)_n$ | Ph | H | Ph | —$(CH_2)_4$— or are each H | |
| (8), (9) | $PPh_2$ | $(CH_2)_n$ | H | Me | Ph | —$(CH_2)_4$— or are each H | |
| (8), (9) | $PPh_2$ | $(CH_2)_n$ | Me | Me | Ph | —$(CH_2)_4$— or are each H | |
| (8), (9) | $PPh_2$ | $(CH_2)_n$ | Bu | Me | Ph | —$(CH_2)_4$— or are each H | |
| (8), (9) | $PPh_2$ | $(CH_2)_n$ | Cy | Me | Ph | —$(CH_2)_4$— or are each H | |
| (8), (9) | $PPh_2$ | $(CH_2)_n$ | i-Pr | Me | Ph | —$(CH_2)_4$— or are each H | |
| (8), (9) | $PPh_2$ | $(CH_2)_n$ | Ph | Me | Ph | —$(CH_2)_4$— or are each H | |
| (8), (9) | $PPh_2$ | $(CH_2)_n$ | H | H | —$(CH_2)_3$— | H | |
| (8), (9) | $PPh_2$ | $(CH_2)_n$ | Me | H | —$(CH_2)_3$— | H | |
| (8), (9) | $PPh_2$ | $(CH_2)_n$ | Bu | H | —$(CH_2)_3$— | H | |
| (8), (9) | $PPh_2$ | $(CH_2)_n$ | Cy | H | —$(CH_2)_3$— | H | |
| (8), (9) | $PPh_2$ | $(CH_2)_n$ | i-Pr | H | —$(CH_2)_3$— | H | |
| (8), (9) | $PPh_2$ | $(CH_2)_n$ | Ph | H | —$(CH_2)_3$— | H | |
| (8), (9) | $PPh_2$ | $(CH_2)_n$ | H | Me | —$(CH_2)_3$— | H | |
| (8), (9) | $PPh_2$ | $(CH_2)_n$ | Me | Me | —$(CH_2)_3$— | H | |
| (8), (9) | $PPh_2$ | $(CH_2)_n$ | Bu | Me | —$(CH_2)_3$— | H | |
| (8), (9) | $PPh_2$ | $(CH_2)_n$ | Cy | Me | —$(CH_2)_3$— | H | |
| (8), (9) | $PPh_2$ | $(CH_2)_n$ | i-Pr | Me | —$(CH_2)_3$— | H | |
| (8), (9) | $PPh_2$ | $(CH_2)_n$ | Ph | Me | —$(CH_2)_3$— | H | |

Where M—L = Rh(CO) or Ru($PPh_3$)Cl; n = 1, 2 or 3; and $Q^3$ & $Q^5$ are each H.
Cy = cyclohexyl

TABLE 4

(10), (11) structures shown with substituents $Q^1$, $Q^2$, $Q^3$, $Q^4$, $Q^5$, $R^4$, $R^6$, M, L, A; formula (11) includes tBuMe$_2$SiO group.

| Formula | A | $Q^2$ | $Q^1$ | $Q^4$ | $R^6$, $R^4$ |
|---|---|---|---|---|---|
| (10), (11) | PPh$_2$ | H | H | H | —(CH$_2$)$_4$— or are each H |
| (10), (11) | PPh$_2$ | Me | H | H | —(CH$_2$)$_4$— or are each H |
| (10), (11) | PPh$_2$ | Bu | H | H | —(CH$_2$)$_4$— or are each H |
| (10), (11) | PPh$_2$ | Cy | H | H | —(CH$_2$)$_4$— or are each H |
| (10), (11) | PPh$_2$ | i-Pr | H | H | —(CH$_2$)$_4$— or are each H |
| (10), (11) | PPh$_2$ | Ph | H | H | —(CH$_2$)$_4$— or are each H |
| (10), (11) | PPh$_2$ | H | Me | H | —(CH$_2$)$_4$— or are each H |
| (10), (11) | PPh$_2$ | Me | Me | H | —(CH$_2$)$_4$— or are each H |
| (10), (11) | PPh$_2$ | Bu | Me | H | —(CH$_2$)$_4$— or are each H |
| (10), (11) | PPh$_2$ | Cy | Me | H | —(CH$_2$)$_4$— or are each H |
| (10), (11) | PPh$_2$ | i-Pr | Me | H | —(CH$_2$)$_4$— or are each H |
| (10), (11) | PPh$_2$ | Ph | Me | H | —(CH$_2$)$_4$— or are each H |
| (10), (11) | PPh$_2$ | H | H | Me | —(CH$_2$)$_4$— or are each H |
| (10), (11) | PPh$_2$ | Me | H | Me | —(CH$_2$)$_4$— or are each H |
| (10), (11) | PPh$_2$ | Bu | H | Me | —(CH$_2$)$_4$— or are each H |
| (10), (11) | PPh$_2$ | Cy | H | Me | —(CH$_2$)$_4$— or are each H |
| (10), (11) | PPh$_2$ | i-Pr | H | Me | —(CH$_2$)$_4$— or are each H |
| (10), (11) | PPh$_2$ | Ph | H | Me | —(CH$_2$)$_4$— or are each H |
| (10), (11) | PPh$_2$ | H | Me | Me | —(CH$_2$)$_4$— or are each H |
| (10), (11) | PPh$_2$ | Me | Me | Me | —(CH$_2$)$_4$— or are each H |
| (10), (11) | PPh$_2$ | Bu | Me | Me | —(CH$_2$)$_4$— or are each H |
| (10), (11) | PPh$_2$ | Cy | Me | Me | —(CH$_2$)$_4$— or are each H |
| (10), (11) | PPh$_2$ | i-Pr | Me | Me | —(CH$_2$)$_4$— or are each H |
| (10), (11) | PPh$_2$ | Ph | Me | Me | —(CH$_2$)$_4$— or are each H |
| (10), (11) | PPh$_2$ | H | H | Ph | —(CH$_2$)$_4$— or are each H |
| (10), (11) | PPh$_2$ | Me | H | Ph | —(CH$_2$)$_4$— or are each H |
| (10), (11) | PPh$_2$ | Bu | H | Ph | —(CH$_2$)$_4$— or are each H |
| (10), (11) | PPh$_2$ | Cy | H | Ph | —(CH$_2$)$_4$— or are each H |
| (10), (11) | PPh$_2$ | i-Pr | H | Ph | —(CH$_2$)$_4$— or are each H |
| (10), (11) | PPh$_2$ | Ph | H | Ph | —(CH$_2$)$_4$— or are each H |
| (10), (11) | PPh$_2$ | H | Me | Ph | —(CH$_2$)$_4$— or are each H |
| (10), (11) | PPh$_2$ | Me | Me | Ph | —(CH$_2$)$_4$— or are each H |
| (10), (11) | PPh$_2$ | Bu | Me | Ph | —(CH$_2$)$_4$— or are each H |
| (10), (11) | PPh$_2$ | Cy | Me | Ph | —(CH$_2$)$_4$— or are each H |
| (10), (11) | PPh$_2$ | i-Pr | Me | Ph | —(CH$_2$)$_4$— or are each H |
| (10), (11) | PPh$_2$ | Ph | Me | Ph | —(CH$_2$)$_4$— or are each H |
| (10), (11) | PPh$_2$ | H | H | —(CH$_2$)$_3$— | H |
| (10), (11) | PPh$_2$ | Me | H | —(CH$_2$)$_3$— | H |
| (10), (11) | PPh$_2$ | Bu | H | —(CH$_2$)$_3$— | H |
| (10), (11) | PPh$_2$ | Cy | H | —(CH$_2$)$_3$— | H |
| (10), (11) | PPh$_2$ | i-Pr | H | —(CH$_2$)$_3$— | H |
| (10), (11) | PPh$_2$ | Ph | H | —(CH$_2$)$_3$— | H |
| (10), (11) | PPh$_2$ | H | Me | —(CH$_2$)$_3$— | H |
| (10), (11) | PPh$_2$ | Me | Me | —(CH$_2$)$_3$— | H |
| (10), (11) | PPh$_2$ | Bu | Me | —(CH$_2$)$_3$— | H |
| (10), (11) | PPh$_2$ | Cy | Me | —(CH$_2$)$_3$— | H |
| (10), (11) | PPh$_2$ | i-Pr | Me | —(CH$_2$)$_3$— | H |
| (10), (11) | PPh$_2$ | Ph | Me | —(CH$_2$)$_3$— | H |

Where M—L = Rh(CO) or Ru(PPh$_3$)Cl; and $Q^3$ & $Q^5$ are each H.

TABLE 5

Structures (12) and (13) shown with Me group, $Q^1$–$Q^5$, $R^4$, $R^6$, M, L, A, Y substituents; (13) includes tBuMe$_2$SiO group.

| Formula | A | Y | $R^4$ | $R^6$ | $Q^4$ | $Q^2$ |
|---|---|---|---|---|---|---|
| (12), (13) | PPh$_2$ | (CH$_2$)$_n$ | H | H | H | C(Me)=CH$_2$ |
| (12), (13) | PPh$_2$ | (CH$_2$)$_n$ | H | H | Me | C(Me)=CH$_2$ |
| (12), (13) | PPh$_2$ | (CH$_2$)$_n$ | H | H | Ph | C(Me)=CH$_2$ |
| (12), (13) | PPh$_2$ | (CH$_2$)$_n$ | —(CH$_2$)$_4$— | | H | C(Me)=CH$_2$ |
| (12), (13) | PPh$_2$ | (CH$_2$)$_n$ | —(CH$_2$)$_4$— | | Me | C(Me)=CH$_2$ |
| (12), (13) | PPh$_2$ | (CH$_2$)$_n$ | —(CH$_2$)$_4$— | | Ph | C(Me)=CH$_2$ |
| (12), (13) | PPh$_2$ | (CH$_2$)$_n$ | H | —(CH$_2$)$_3$— | | C(Me)=CH$_2$ |
| (12), (13) | PPh$_2$ | (CH$_2$)$_n$ | H | —(CH$_2$)$_3$— | | CHMe$_2$ |
| (12), (13) | PPh$_2$ | (CH$_2$)$_n$ | H | H | H | CHMe$_2$ |
| (12), (13) | PPh$_2$ | (CH$_2$)$_n$ | H | H | Me | CHMe$_2$ |
| (12), (13) | PPh$_2$ | (CH$_2$)$_n$ | H | H | Ph | CHMe$_2$ |
| (12), (13) | PPh$_2$ | (CH$_2$)$_n$ | —(CH$_2$)$_4$— | | H | CHMe$_2$ |
| (12), (13) | PPh$_2$ | (CH$_2$)$_n$ | —(CH$_2$)$_4$— | | Me | CHMe$_2$ |
| (12), (13) | PPh$_2$ | (CH$_2$)$_n$ | —(CH$_2$)$_4$— | | Ph | CHMe$_2$ |

Where M—L = Rh(CO) or Ru(PPh$_3$)Cl; n = 1, 2 or 3; and $Q^1$, $Q^3$ & $Q^5$ are each H.

TABLE 6

Structures (14) and (15) shown with Me group, $Q^1$–$Q^5$, $R^4$, $R^6$, M, L, A substituents; (15) includes tBuMe$_2$SiO group.

| Formula | A | $R^4$ | $R^6$ | $Q^4$ | $Q^2$ |
|---|---|---|---|---|---|
| (14), (15) | PPh$_2$ | H | H | H | C(Me)=CH$_2$ |

TABLE 6-continued (14)

(15)

| Formula | A | R⁴ | R⁶ | Q⁴ | Q² |
|---|---|---|---|---|---|
| (14), (15) | PPh₂ | H | H | Me | C(Me)=CH₂ |
| (14), (15) | PPh₂ | H | H | Ph | C(Me)=CH₂ |
| (14), (15) | PPh₂ | —(CH₂)₄— | | H | C(Me)=CH₂ |
| (14), (15) | PPh₂ | —(CH₂)₄— | | Me | C(Me)=CH₂ |
| (14), (15) | PPh₂ | —(CH₂)₄— | | Ph | C(Me)=CH₂ |
| (14), (15) | PPh₂ | H | —(CH₂)₃— | | C(Me)=CH₂ |
| (14), (15) | PPh₂ | H | H | H | CHMe₂ |
| (14), (15) | PPh₂ | H | H | Me | CHMe₂ |
| (14), (15) | PPh₂ | H | H | Ph | CHMe₂ |
| (14), (15) | PPh₂ | —(CH₂)₄— | | H | CHMe₂ |
| (14), (15) | PPh₂ | —(CH₂)₄— | | Me | CHMe₂ |
| (14), (15) | PPh₂ | —(CH₂)₄— | | Ph | CHMe₂ |
| (14), (15) | PPh₂ | H | —(CH₂)₃— | | CHMe₂ |

Where M—L = Rh(CO) or Ru(PPh₃)Cl; and Q¹, Q³ & Q⁵ are each H

The compounds of formula (1) can be prepared by one of the following procedures. References to compounds of formula (16) include all double bond isomers within the cyclopentadiene ring.

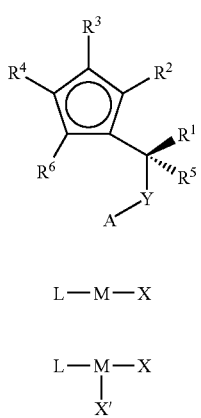

(16)

L—M—X (17)

L—M—X
    |
    X' (18)

The compounds of formula (1) can be prepared by deprotonating a compound of formula (16) (for example with a butyllithium) in a suitable solvent (such as tetrahydrofuran) and reacting the product obtained with a compound of formula (17) (wherein X is a suitable leaving group such as a halogen atom).

In the case where A=NR¹, compounds of Formula (1) can be prepared by doubly deprotonating a compound of formula (16) (for example with 2 equivalents of butyllithium) in a suitable solvent (such as tetrahydrofuran) and reacting the product obtained with a compound of formula (18) (wherein X and X' are suitable leaving groups such as halogen atoms).

Alternatively the compounds of formula (1) can be prepared by reacting a compound of formula (16) in a suitable solvent (such as toluene) with a compound of formula (17) or (18) (wherein X and X' are suitable leaving groups such as a halogen atoms).

Alternatively the compounds of formula (1) can be prepared by reacting a trialkylsilyl or trialkylstannyl derivative of a compound of formula (16) (obtained by replacing one hydrogen on the cycopentadienyl ring with a trialkylsilyl or trialkylstannyl) in a suitable solvent (such as toluene) with a compound of formula (17) or (18) (wherein X and X' are suitable leaving groups such as a halogen atoms).

Alternatively, when R² and R³ join to form a saturated 6 member carbocyclic ring (for example ($\eta^5$:$\eta^1$-4,5,6,7-tetrahydroindenyl-CH(Cy)CH₂PPh₂)Ru$^{II}$(Cl)(PPh₃)), a compound of formula (1) can be prepared hydrogenating a compound of formula (1) wherein R² and R³ join to form an aromatic ring (such as ($\eta^5$:$\eta^1$-indenyl-CH(Cy)CH₂PPh₂)Ru$^{II}$(Cl)(PPh₃)) under suitable conditions (such as with hydrogenation at between room temperature and 100° C., at between 1 and 100 bar (1 bar=1 atmosphere; 760 mm Hg) using a suitable catalyst (such as platinum oxide) in a suitable solvent (such as dichloromethane)).

The compounds of the invention can be used as catalysts in a variety of different industrial processes from which chiral products are required. Examples of such processes are: hydride transfers (such as hydrogenations of chain or cyclic alkenes, imines, enamines, or ketones, hydrosilation of imines or ketones); hydroboration or hydrosilation of alkenes; co-cyclisation of two alkenes or an alkene and an alkyne; carbometallation of alkenes, and catalytic processes in which carbometallation of alkenes is a key step (i.e. formation of carbon—carbon bonds to alkenes); 'Pauson Khand cyclisations (co-cyclisation of an alkene, alkyne, and carbon monoxide to form a cyclopentenone); allylic displacements; Nozaki-Hiyama additions (reaction of an organic halide an aldehyde, and stoichiometric metal to form a secondary alcohol); epoxidations; 1,2-dihydroxylations; 1,2-aminohydroxylations; 1,2-dithiolations; aminations (replacement of a C—H bond with a C—N bond); cyclopropanations; pinacol couplings (addition of two carbonyl compounds to afford a 1,2-diol); Diels Alder cycloadditions; hetero-Diels-Alder cycloadditions; [2+2+2]-cycloadditions; isomerisations; cycloisomerisations; addition of enolsilanes or allylsilanes to aldehydes or imines; hydroformylation of alkenes.

The following Examples illustrate the invention.

All NMR data is expressed in ppm from tetramethylsilane.

Throughout the Examples the following abbreviations are used:

THF=tetrahydrofuran;
NMR=Nuclear Magnetic Resonance; ppm=parts per million; s=singlet; d=doublet m multiplet; t=triplet; q=quartet; dd=doublet of doublets; dt=doublet of triplets; brs=broad singlet; ddd=doublet of doublet of doublets; mp=melting point;
DME=dimethoxyethane;
eq=equivalents;
HMPA=hexamethylphosphoramide ((CH$_3$)$_2$N)}PO.

Synthesis of ($\eta^6$:$\eta^1$-Indenyl-CH(Cy)CH$_2$PPh$_2$)Rh$^1$CO

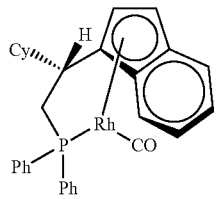

To a solution of [(2R)-2-cyclohexyl-2-(3H-inden-1-yl)ethyl]diphenylphosphine (0.41 g, 1 mmol) in THF (20 mL) under argon at −78° C., was added slowly n-BuLi (0.4 mL of a 2.5 M solution in hexanes, 1.0 mmol), and the reaction stirred at −78° C. for 30 min, then allowed to warm to room temperature and stirred for a further 2 h. The dark red ligand anion solution was then cooled to −78° C. and added via cannula dropwise over ca. 20 min to a solution of [Rhi(μ-Cl)(CO)$_2$]$_2$ (194 mg, 0.5 mmol) in THF (20 mL) at −78° C., immediately forming a dark brown solution. This solution was allowed to stir at −78° C. for 2 h before being warmed slowly to room temperature, overnight (16 h). The solvents were then removed in vacuo, to give a brown foamy solid. $^1$H NMR spectroscopy showed the desired complex formed as a 78:22 mixture of diastereoisomers. The crude material was purified by column chromatography (neutral alumina, 30–50% toluene in petrol) to afford the product as an orange powder (367 mg, 68%). Recrystallization from diethyl ether/hexane at −30° C. afforded the major diastereoisomer as clear red crystals (195 mg, 36%).

Mpt. decomposes 168° C. (sealed tube).
[a]$_D$$^{21}$−75.6 (c=1, CHCl$_3$).
$^1$H NMR (400 MHz, C$_6$D$_6$) δ 7.75–7.68 (2H, m), 7.59 (2H, ddd, J$_{HP}$=11.7 Hz, J$_{HH}$=7.8, 1.7 Hz), 7.38 (1H, d+fs, J$_{HH}$=8.0 Hz), 7.21–7.17 (4H, m), 7.12–7.08 (3H, m), 7.07 (1H, ddd, J$_{HH}$=8.0, 7.0, 1.0 Hz), 6.98 (1H, d+fs, J$_{HH}$=8.0 Hz), 6.20 (1H, dd, J$_{HH}$=2.8 Hz, J$_{HP}$*=2.7 Hz), 6.14 (1H, dd, J$_{HH}$=2.8 Hz, J$_{HP}$*=2.5 Hz), 3.30 (1H, dddd, J$_{HP}$=13.3 Hz, J$_{HH}$=13.3, 4.6 Hz, J$_{HRh}$=2.5 Hz), 2.93 (1H, ddd, J$_{HH}$=13.6, 13.3 Hz, J$_{HP}$=7.0 Hz), 2.63 (1H, dddd, J$_{HH}$=13.6, 4.6, 4.6 Hz, J$_{HP}$=9.0 Hz), 1.80–0.72 (11H, m) ppm. *—could be coupling to Rh. $^{13}$C NMR (100 MHz, C$_6$D$_6$): δ 191.26 (C, J$_{PC}$=17.9 Hz, J$_{RhC}$=88.4), 136.25 (C, J$_{PC}$=44.6 Hz, J$_{RhC}$=3.5), 134.42 (C, J$_{PC}$=38.4 Hz, J$_{RhC}$=1.0), 134.48 (CH, J$_{PC}$=13.8 Hz, J$_{RhC}$=1.0), 131.72 (CH, J$_{PC}$=11.6 Hz, J$_{RhC}$=1.2), 128.44 (CH, J$_{PC}$=10.6 Hz), 128.50 (CH, J$_{PC}$=10.4 Hz), 130.52 (CH, J$_{PC}$=2.4 Hz), 129.82 (CH, J$_{PC}$=2.4 Hz), 124.37 (CH, J$_{PC}$=0.7 Hz), 121.09 (CH), 116.41 (C, J$_{PC}$=2.3 Hz, J$_{RhC}$=1.4 Hz), 117.92 (CH, J$_{PC}$=1.2 Hz), 116.08 (C, J$_{PC}$=1.1 Hz, J$_{RhC}$=0.9 Hz), 117.42 (CH), 103.23 (C, J$_{PC}$=5.0 Hz, J$_{RhC}$=3.8 Hz), 91.36 (CH, J$_{PC}$=5.6 Hz, J$_{RhC}$=3.1 Hz), 76.09 (CH, J$_{PC}$=10.6 Hz, J$_{RhC}$=3.6 Hz), 52.60 (CH$_2$, J$_{PC}$=29.7 Hz), 42.95 (CH, J$_{PC}$=22.4 Hz), 39.37 (CH, J$_{PC}$=4.8 Hz), 33.56 (CH$_2$), 31.17 (CH$_2$), 26.58 (CH$_2$), 26.42 (CH$_2$), 26.25 (CH$_2$). J$_{RhC}$ and J$_{RhC}$ may be interchanged.

IR (CH$_2$Cl$_2$ solution): 2929 (m), 2853 (m), 1939 (s, CO), 1479 (w), 1436 (w), 1095 (w) cm$^{-1}$.

LRMS (AP$^+$) m/z 554 ((M+CH$_3$CN+H—CO)$^+$, 100%), 553 ((M+CH$_3$CN—CO)$^+$, 46), 541 ((M+H)$^+$, 33), 513 ((M+H—CO)$^+$, 10), 512 ((M—CO)$^+$, 4).

Anal. Calcd. for C$_{30}$H$_{30}$OPRh: C, 66.67; H, 5.60; P, 5.73. Found: C, 66.71; H, 5.67; P, 5.67%

Synthesis of ($\eta^5$: $\eta^1$-Indenyl-CH(Cy)CH$_2$PPh$_2$)Ru$^{11}$(Cl)(PPh$_3$)

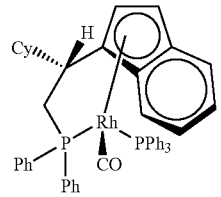

[(2R)-2-Cyclohexyl-2-(1H-3-indenyl)ethyl](diphenyl)phosphine (1.0 eq, 3.0 mmol, 1.23 g) was dissolved in toluene (90 mL) and cooled under argon to −78° C. n-BuLi (2.5 M solution in hexanes, 1.1 eq, 3.3 mmol, 1.3 mL) was then added dropwise to the stirred solution, with the exclusion of light. The reaction was stirred at −78° C. for 15 minutes, then allowed to warm slowly to room temperature, and stirred for two hours.

Meanwhile a suspension of dichlorotris(triphenylphosphine)ruthenium(II) (1.1 eq, 3.3 mmol, 3.16 g) in THF (30 mL) was prepared and cooled to −60° C., under argon. The anion solution was then added dropwise to the ruthenium solution, via canula. The resulting dark mixture was stirred at −60° C. for 15 minutes, then warmed gradually to 95° C. and stirred at this temperature overnight (ca. 17 hours). The dark solution was cooled to room temperature and the solvents removed in vacuo, to give a brown solid. The complex was purified by column chromatography (Al$_2$O$_3$, 50->60% diethylether/petrol) using degassed solvents, to give the title complex as a brown air stable powder (2.02 g, 2.5 mmol, 83%).

$^1$H NMR (400 MHz, C$_6$D$_6$): δ/ppm=8.29 (2H, dd, J=10.0, 9.0 Hz), 7.84 (5H, br.m), 7.47 (1H, dd, J=10.8, 4.8 Hz), 7.41 (1H, d, J=8.0 Hz), 7.34 (2H, td, J=7.5, 1.0 Hz), 7.23 (2H, m), 7.17 (2H, m), 7.05 (10H, br.m), 6.94 (1H, td, J=7.7, 1.5 Hz), 6.87 (1H, t+fs, J=7.4 Hz), 6.75 (2H, td, J=7.5, 1.2 Hz), 5.04 (1H, d, J=1.3 Hz), 3.47 (1H, ddd, J=12.0, 12.0, 4.5 Hz), 2.85 (1H, ddd, J=13.0, 13.0, 4.9 Hz), 2.46 (1H, dddd, J=13.0, 8.7, 4.4, 4.4 Hz), 2.28 (1H, dd, J=1.9, 1.9 Hz), 1.38–1.73 (5H, m), 1.10–1.20 (2H, m), 0.565–0.97 (4H, m).

$^{13}$C NMR (100 MHz, C$_6$D$_6$): δ/ppm=139.76 (C, d, J=26.6 Hz), 139.73 (C, d, J=26.1 Hz), 139.71 (C, d, J=25.9 Hz), 139.12 (C, v.br.d, J=37.2 Hz), 138.51 (C, d, J=30.0 Hz), 135.60 (2×CH, d, J=10.6 Hz), 134.23 (5×CH, v.br.s), 131.53 (2×CH, d, J=9.2 Hz), 129.93 (CH, dd, J=2.0, 2.0 Hz), 129.87 (CH, d, J=1.9 Hz), 128.91 (2×CH, d, J=1.4 Hz), 128.30 (CH, s+fs), 128.11 (CH, d, J=9.2 Hz), 128.09 (CH, s), 127.97 (2×CH, d, J=9.2 Hz), 127.82 (2×CH, d, J=8.7 Hz), 127.77 (6×CH, d, J=9.4 Hz), 127.65 (CH, d, J=2.9 Hz), 123.80 (CH, d, J=2.9 Hz), 121.93 (CH, s+fs), 106.96 (C, dd, J=4.4, 1.0

Hz), 106.42 (C, dd, J=6.0, 1.9 Hz), 94.26 (C, dd, J=11.6, 2.4 Hz), 74.59 (CH, dd, J=6.8, 2.4 Hz), 66.65 (CH, s), 51.21 ($CH_2$, d, J=32.9 Hz), 42.53 (CH, d, J=19.8 Hz), 37.53 (CH, d, J=4.8 Hz), 33.45 ($CH_2$, s), 31.14 ($CH_2$, s), 26.43 ($CH_2$, s), 26.18 ($CH_2$, s), 26.07 ($CH_2$, s).

$^{31}$P NMR (120 MHz, $C_6D_6$, proton decoupled): δ/ppm=47.95 (d, $J_{PP}$=26.4 Hz), 38.96 (d, $J_{PP}$=26.4 Hz).

IR (solid): v=3053 (m), 2926 (m), 2849 (m), 1481 (m), 1434 (s), 1265 (w), 1185 (m), 1092 (s) $cm^{-1}$ LRMS ($ES^+$): m/z=808.1 $(M)^+$, 773.2 $(M—Cl)^+$ $[α]_D^{21}$=−160 (c=0.05, $CHCl_3$)

Anal. Calcd. for $C_{47}H_{45}ClP_2Ru$: C, 69.84; H, 5.61; Cl, 4.39; P, 7.66; Found: C, 69.74; H, 5.64; Cl, 4.29; P, 7.61.

Synthesis of ($η^5$:$η^1$-4,5,6,7-tetrahydroindenyl-CH(Cy)$CH_2PPh_2$)$Ru^{11}$(Cl)($PPh_3$)

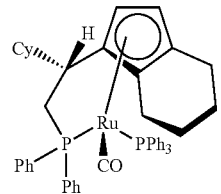

A suspension of ($μ^5$:$μ^1$-indenyl-CH(Cy)$CH_2PPh_2$)$Ru^{11}$(Cl)($PPh_3$) 3 (0.40 g, 0.5 mmol) and $PtO_2$ (12 mg, 10 mol %) was prepared in dichloromethane (20 mL) and the mixture was then degassed by freezing (liquid $N_2$), evacuating to 0.05 mmHg then thawing in a closed system and refilling with argon (this degassing cycle was repeated 3 times).

The degassed suspension was transferred, via syringe, to a high-pressure stainless steel bomb (argon-filled), and a high-pressure $H_2$ cylinder attached. The bomb was pressurised to 1800 psi $H_2$ and sealed, then heated in an oil bath, to 65° C. (which caused an increase in pressure to ~1850 psi). The reaction was stirred under these conditions for 3 days.

After depressurising the bomb, the reaction mixture was filtered through celite with further dichloromethane (3×5 mL), to remove $PtO_2$ catalyst. Concentration of the light brown solution then gave a pale brown/orange solid (406 mg, 0.5 mmol, 99%), shown by NMR to be >90% title complex. Further purification by column chromatography ($Al_2O_3$, 30% diethylether/petrol) using degassed solvents gave the title complex as a pale orange solid, at reduced yield (164 mg, 0.2 mmol, 40%).

$^1$H NMR (400 MHz, $C_6D_6$): δ/ppm=8.67 (2H, dd, J=9.9, 8.4 Hz), 7.79 (5H, v.br.s), 7.38 (2H, t+fs, J=7.4 Hz), 7.19–7.26 (3H, m), 7.06 (10H, v.br.s), 6.87 (1H, t+fs, J=7.5 Hz), 6.76 (2H, td, J=7.6, 1.5 Hz), 4.53 (1H, d, J=1.6 Hz), 3.39 (1H, ddd, J=11.8 Hz, 11.8, 4.4 Hz), 3.28 (1H, ddd, J=21.1, 10.7, 5.3 Hz), 2.70 (1H, ddd, J=12.6, 12.6, 4.8 Hz), 2.68–2.76 (2H, m), 2.47–2.55 (1H, m), 2.39 (1H, d, J=2.0 Hz), 2.28–2.39 (2H, m), 2.05 (1H, dddd, J=13.3, 8.9, 4.4, 4.4 Hz), 0.70–1.92 (13H, m).

$^{13}$C NMR (100 MHz, $C_6D_6$): δ/ppm=139.31 (C, d, J=28.3 Hz), 139.30 (C, d, J=28.3 Hz), 139.15 (C, d, J=26.1 Hz), 139.12 (C, d, J=26.1 Hz), 135.24 (2×CH, d, J=10.9 Hz), 134.09 (5×CH, v.br.s), 131.54 (2×CH, d, J=9.2 Hz), 129.81 (CH, d, J=2.2 Hz), 128.74 (CH, s+fs), 128.73 (CH, s+fs), 128.30 (CH, s+fs), 128.12 (2×CH, d, J=9.2 Hz), 127.73 (2×CH, d, J=8.9 Hz), 127.70 (6×CH, d, J=9.2 Hz), 127.69 (2×CH, d, J=10.5 Hz), 110.92 (C, dd, J=3.9, 1.2 Hz), 100.67 (C, dd, J=8.0, 1.9 Hz), 89.39(C, dd, J=14.0, 2.2 Hz), 80.39 (CH, d, J=6.5 Hz), 59.08 (CH, s), 50.55 ($CH_2$, d, J=33.3 Hz), 42.88 (CH, d, J=19.1 Hz), 37.28 (CH, d, J=5.1 Hz), 33.44 ($CH_2$, s), 31.33 ($CH_2$, s), 26.53 ($CH_2$, s), 26.41 ($CH_2$, s), 26.18 ($CH_2$, s), 24.09 ($CH_2$, s), 23.45 ($CH_2$, s), 22.70 ($CH_2$, s), 21.55 ($CH_2$, s). 1 quaternary carbon (expected as a very broad signal around 139) not observed.

$^{31}$P NMR (162 MHz, $C_6D_6$, proton decoupled): δ/ppm=43.86 (d, $J_{PP}$=39.0 Hz), 37.54 (d, $J_{PP}$=39.0 Hz).

IR (solid): v=2932 (m), 2858 (m), 1482 (m), 1433 (s), 1091(s) $cm^{-1}$

LRMS (ES+): m/z=812.3 $(M)^+$

Synthesis of rac-($η^5$:$η^1$-Indenyl-CH(Ph)CH(Ph)$PPh_2$)$Ru^{11}$($PPh_3$)Cl

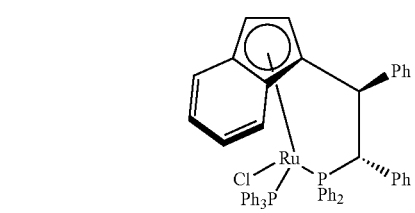

A solution of the crude lithium salt of rac-[2-(3H-inden-1-yl)-1,2-diphenylethyl]diphenyl-phosphane (~1.0 mmol, 480 mg) was prepared in toluene (33 mL) and transferred slowly (over ca. 15 minutes) via syringe, to a suspension of dichlorotris(triphenylphosphine)ruthenium(II) (1.2 mmol, 1.15 g) in toluene (19 mL) at −60° C. The resulting dark mixture was stirred at −60° C. for 15 minutes, then warmed gradually to 95° C. and stirred at this temperature for 24 hours.

After this time, the reaction was cooled to room temperature and the solvents removed in vacuo, to give a dark solid. $^1$H NMR of the crude confirmed the title complex had been prepared as a 72:28 mixture of planar-chiral diastereoisomers with very high metal centred diastereoselectivity—ca. 97:1.

The complex was purified by flushing an ethereal solution through a pad of deactivated $Al_2O_3$, in order to remove inorganic salts, then column chromatography (neutral $Al_2O_3$, 50% diethyl ether/petrol) using degassed solvents, to give a yellow/light brown powder (223 mg, 0.25 mmol, 25% over two steps, from spirocycle 2,3-diphenylspiro[cyclopropane-1,1'-indene] precursor).

$^1$H NMR (400 MHz, $C_6D_6$, major isomer): δ/ppm=7.93 (2H, t, J=7.9 Hz), 7.81 (1H, d, J=8.5 Hz), 7.55–7.76 (5H, v.br.s), 7.48 (2H, t, J=8.0 Hz), 7.43 (1H, t, J=7.7 Hz), 7.12–7.33 (7H, m), 6.99–7.12 (9H, v.br.s), 6.97 (3H, t, J=7.7 Hz), 6.67–6.90 (9H, m), 5.25 (1H, dd, J=13.3, 5.5 Hz), 4.88 (1H, br.s), 4.82 (1H, dd, J=13.3, 5.5 Hz), 3.47 (1H, d, J=2.5 Hz).

$^{31}$P NMR (121 MHz, $C_6D_6$): δ/ppm=55.50 (d, J=19.5 Hz, minor isomer), 52.80 (d, J=20.8 Hz, major isomer).

Synthesis of rac-($\eta^5$:$\eta^1$-Indenyl-CH(Ph)CH(Ph)PPh$_2$)Rh$^1$CO

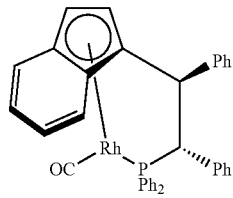

A solution of the crude lithium salt of rac-[2-(3H-inden-1-yl)-1,2-diphenylethyl]diphenyl-phosphane (~0.5 mmol, 240 mg) was prepared in THF (5 mL) and cooled to −40° C. The ligand solution was then transferred dropwise via canula (over 30 minutes), to a brick-red suspension of [Rh$_I$(μ-Cl)(CO)$_2$]$_2$ (0.6 mmol, 233 mg) in THF, at −78° C. The mixture was stirred at −78° C. for 40 minutes, then warmed slowly to room temperature, with stirring, over 16 hours. The solvents were then removed in vacuo, to give a dark-red foamy solid.

Crude $^1$H NMR showed new resonances at δ=5.27 ppm and δ=4.61 ppm consistent with Cp-resonances in previous rhodium complexes, suggesting the desired complex had been formed. $^{31}$P NMR of the crude showed minor and major resonances at δ=46.14 ppm and δ=45.84 ppm, with similar Rh—P coupling constants to previous rhodium complexes, and integration showed the complex had formed as a 70:30 mixture of diastereoisomers.

However, attempted purification of the crude complex by column chromatography (neutral Al$_2$O$_3$, 60% diethyl ether/petrol) failed to yield any clean material, and it is likely the complex was unstable to chromatography.

$^{31}$P NMR (121 MHz, C$_6$D$_6$, crude): δ/ppm=46.14 (d, J=177.7 Hz, major isomer), 45.84 (d, J=175.4 Hz, minor isomer).

Synthesis of rac-($\eta^5$:$\eta^1$-Indenyl-CH(Cy)CH$_2$CH$_2$PPh$_2$)Ru$^{II}$(PPh$_3$)Cl

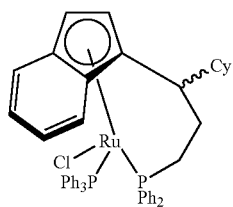

Ligand rac-[3-Cyclohexyl-3-(3H-inden-1-yl)propyl]diphenyl-phosphane (425 mg, 1.0 mmol) was dissolved in toluene (33 mL) and cooled to −78° C. n-BuLi (2.5 M solution in hexanes, 0.44 mL, 1.1 mmol) was added dropwise, in the dark, and the reaction stirred at −78° C. for 15 minutes. The resulting cloudy suspension was then warmed slowly to room temperature and stirred for 2 hours, to give a yellow solution. This solution was transferred slowly (over ca. 10 minutes) via syringe, to a suspension of dichlorotris(triphenylphosphine)ruthenium(II) (1.1 mmol, 1.1 g) in toluene (19 mL) at −60° C.

The dark mixture was stirred at −60° C. for 15 minutes, then warmed to reflux for 24 hours. After this time, the reaction was cooled to room temperature and the solvents removed under vacuum. $^1$H NMR of the crude material indicated the expected complex had been formed as a 83:17 mixture of planar-chiral diastereoisomers, with complete metal-centre control (no further diastereoisomer resonances seen).

Inorganics were removed from the crude by redissolving the material in diethyl ether/toluene and flushing the mixture through a short pad of Al$_2$O$_3$ (neutral, deactivated). Final purification of the complex was achieved by column chromatography (30–40% diethyl ether/petrol, neutral Al$_2$O$_3$, using degassed solvents) which provided both diastereoisomers of the complex. The major isomer was collected as a dark-red solid (454 mg, 0.55 mmol, 55%, R$_f$ 0.4 in 40% diethyl ether/petrol), the minor isomer was collected as a red/brown solid (70 mg, 0.08 mmol, 9%, R$_f$ 0.1 in 40% diethyl ether/petrol).

The minor isomer crystallised from a solution in diethyl ether on standing at room temperature for 3 hours. The major isomer was crystallised by slow diffusion of pentane into a solution in benzene, over 2 weeks at 4° C.

Major Diastereoisomer:

$^1$H NMR (400 MHz, C$_8$D$_6$): δ/ppm 7.75 (1H, d, J=8.5 Hz), 7.61(1H, d, J=7.6 Hz), 7.59 (2H, dd, J=9.8, 2.0 Hz), 7.57 (4H, dd, J=9.8, 4.0 Hz), 7.34 (2H, dd, J=8.4, 8.4 Hz), 7.28 (1H, d, J=7.8 Hz), 7.24 (2H, dd+fs, J=7.6, 7.6 Hz), 7.18 (2H, dd, J=7.5, 7.5 Hz), 6.95–7.03 (10H, m), 6.88 (1H, dd, J=7.4, 7.4 Hz), 6.83 (1H, d, J=7.3 Hz), 6.71 (2H, dd+fs, J=7.3, 7.3 Hz), 4.65 (1H, s+fs), 3.90 (1H, dddd, J=13.3, 13.3, 7.3, 1.5 Hz), 3.60 (1H, d+fs, J=12.1 Hz), 3.36 (1H, br.s), 2.65 (1H, ddd, J=14.4, 14.4, 5.6 Hz), 2.09 (1H, dddd, J=36.0, 14.6, 2.9, 2.9 Hz), 1.48–1.75 (6H, m), 0.88–1.20 (6H, m).

$^{13}$C NMR (100 MHz, C$_6$D$_6$): 139.32 (C, d, J$_{CP}$=39.1 Hz), 138.88 (3×C, d, J$_{CP}$=35.2 Hz), 137.47 (C, d, J$_{CP}$=43.2 Hz), 135.28 (CH, d, J$_{CP}$=9.7 Hz), 133.69 (3×CH, d, J$_{CP}$=10.9 Hz), 133.28 (CH, d, J$_{CP}$=7.5 Hz), 129.98 (CH, d, J$_{CP}$=2.2 Hz), 128.38 (CH, d, J$_{CP}$=2.4 Hz), 128.30 (CH, s), 128.17 (3×CH, d, J$_{CP}$=1.9 Hz), 127.89 (CH, d, J$_{CP}$=9.7 Hz), 127.61 (3×CH, d, J$_{CP}$=9.0 Hz), 127.19 (CH, d, J$_{CP}$=9.0 Hz), 125.81 (CH, s), 125.73 (CH, s), 123.93 (CH, s), 110.67 (C, dd, J$_{CP}$=3.6, 1.5 Hz), 105.53 (C, d, J$_{CP}$=7.3 Hz), 84.18 (CH, s), 75.06 (C, dd, J$_{CP}$=13.5, 1.1 Hz), 64.38 (CH, d, J$_{CP}$=1.2 Hz), 45.68 (CH, d, J$_{CP}$=4.9 Hz), 40.06 (CH, d, J$_{CP}$=2.2 Hz), 30.59 (CH$_2$, s), 30.46 (CH$_2$, s), 30.37 (CH$_2$, dd, J$_{CP}$=35.4, 1.1 Hz), 27.07 (CH$_2$, s), 27.01 (CH$_2$, s), 26.71 (CH$_2$, s), 26.22 (CH$_2$, s).

$^{31}$P NMR (121 MHz, C$_6$D$_6$): δ/ppm=48.75 (d, J=35.7 Hz), 38.72 (d, J=35.7 Hz).

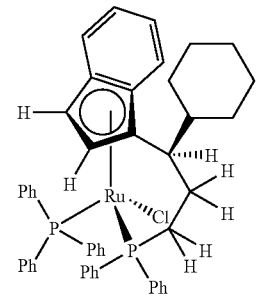

Major isomer

83:17

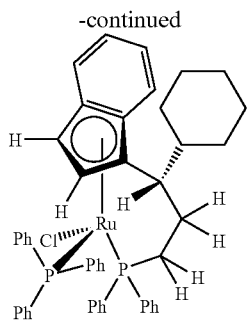

Minor isomer

Minor Diastereoisomer:

$^1$H NMR (400 MHz, C$_6$D$_6$): δ/ppm=7.76 (1H, dd, J=8.9, 8.9 Hz), 7.65–7.73 (6H, m), 7.56 (1H, d, J=8.5 Hz), 7.33 (1H, dd, J=7.4, 7.4 Hz), 7.19–7.35 (6H, m), 6.97–7.09 (10H, m), 6.81 (1H, dd, J=8.5, 8.5 Hz), 6.79 (1H, dd, J=7.8, 7.8 Hz), 6.59 (1H, dd, J=8.5, 8.5 Hz), 6.54 (1H, d, J=8.3 Hz), 4.90 (1H, s+fs), 4.38 (1H, s+fs), 2.69 (1H, ddd, J=14.1, 14.1, 5.3 Hz), 2.12 (1H, dddd, J=35.3, 14.2, 2.7, 2.7), 1.97 (1H, dd, J=12.3, 12.3 Hz), 1.88 (1H, br.d, J=13.6 Hz), 1.79 (1H, dddd, J=13.8, 13.8, 2.4, 2.4 Hz), 1.76 (1H, d+fs, J=14.3 Hz), 1.59 (1H, d+fs, J=12.1 Hz), 1.18–1.54 (4H, m), 1.06 (1H, ddddd, J=12.3, 12.3, 12.3, 3.2, 3.2 Hz), 0.82–1.02 (3H, m), 0.71 (1H, dddd, J=12.1, 12.1, 12.1, 3.1 Hz).

$^{13}$C NMR (100 MHz, C$_6$D$_6$): 141.90 (C, d, J$_{CP}$=29.6 Hz), 138.89 (3×C, d, J$_{CP}$=35.2 Hz), 137.50 (C, d, J$_{CP}$=43.2 Hz), 134.71 (3×CH, d, J$_{CP}$=9.7 Hz), 132.40 (CH, d, J$_{CP}$=9.7 Hz), 131.96 (CH, d, J$_{CP}$=8.3 Hz), 131.55 (CH, d, J$_{CP}$=2.7 Hz), 129.15 (3×CH, d, J$_{CP}$=0.7 Hz), 128.87 (CH, d, J$_{CP}$=5.6 Hz), 128.11 (CH, d, J$_{CP}$=10.0 Hz), 127.80 (CH, d, J$_{CP}$=8.3 Hz), 127.46 (3×CH, d, J$_{CP}$=9.5 Hz), 125.82 (CH, s), 125.65 (CH, s), 125.18 (CH, s), 124.61 (CH, s), 119.24 (C, dd, J$_{CP}$=3.0, 1.6 Hz), 101.13 (C, dd, J$_{CP}$=8.5, 1.0 Hz), 83.22 (CH, s), 72.64 (CH, d, J$_{CP}$=3.4 Hz), 70.78 (C, d, J$_{CP}$=13.9 Hz), 44.31 (CH, s), 42.64 (CH, s), 32.13 (CH$_2$, s), 31.75 (CH$_2$, s), 29.76 (CH$_2$, d, J$_{CP}$=37.2 Hz), 26.68 (CH$_2$, s), 26.62 (CH$_2$, s), 26.56 (CH$_2$, s), 25.55 (CH$_2$, s).

$^{31}$P NMR (121 MHz, C$_6$D$_6$): δ/ppm=57.35 (d, J=41.4 Hz), 26.76 (d, J=41.4 Hz).

Synthesis of rac-($\eta^5$:$\eta^1$-Indenyl-CH(Cy) CH$_2$CH$_2$PPh$_2$)Rh$^1$CO

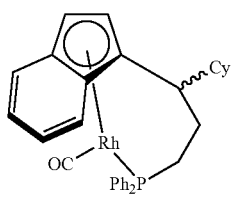

Ligand rac-[3-Cyclohexyl-3-(3H-inden-1-yl)propyl] diphenyl-phosphane (212 mg, 0.5 mmol) was dissolved in THF (5 mL) and cooled to −78° C., under argon. n-BuLi (2.5 M solution in hexanes, 0.22 mL, 0.55 mmol) was added to the cold ligand solution, in the dark. The reaction was stirred at −78° C. for 30 minutes, then warmed to room temperature and stirred for 2 hours. The ligand anion solution was then cooled to −78° C., and added slowly via cannula, to a −78° C. solution of [Rh$^1$(μ-Cl)(CO)$_2$]$_2$ (107 mg, 0.27 mmol) in THF (5 mL). The resulting dark red suspension was stirred at −78° C. for a further 30 minutes, then warmed slowly to room temperature over 14 hours. Solvents were now removed in vacuo, to give a crude reddish-brown solid. $^{31}$P NMR showed complex had formed in a 74:26 mixture of diastereoisomers. The crude material was purified by column chromatography (neutral Al$_2$O$_3$, 4–6% diethyl ether in petrol) to give a yellow film (44.9 mg, 0.08 mmol, 16%).

The $^1$H NMR spectrum shows a ca. 3:1 mixture of diastereoisomers, resonances from the major isomer have been identified and listed below, followed by a list of remaining resonances attributed to the minor isomer by integration.

$^1$H NMR (400 MHz, C$_6$D$_6$, major diastereoisomer): δ/ppm=7.64 (2H, ddd, J=11.1, 8.1, 1.3 Hz), 7.38–7.44 (3H, m), 6.97–7.19 (9H, m), 6.04 (1H, dd, J=3.8, 3.1 Hz, Cp-H), 5.96 (1H, dd, J=2.7, 2.4 Hz, Cp-H), 2.42 (1H, ddd, J=14.3, 14.3, 6.4 Hz), 2.11 (1H, ddd, J=9.8, 9.8, 2.1 Hz), 1.84 (1H, dd, J=36.2, 12.6 Hz), 1.51–1.83 (5H, m), 1.09–1.50 (5H, m), 0.83–1.05 (3H, m).

$^1$H NMR (400 MHz, C$_6$D$_6$, remaining minor resonances): δ/ppm=7.47 (2H, ddd, J=11.1, 7.9, 1.5 Hz), 7.34 (1H, dd, J=11.1, 1.7 Hz), 7.33 (1H, dd, J=11.2, 2.3 Hz), 6.90 (1H, t, J=7.8 Hz), 6.72 (1H, d, J=8.2 Hz), 6.00 (1H, dd, J=4.1, 3.1 Hz, Cp-H), 5.95 (1H, dd, J=2.7, 2.4 Hz, Cp-H).

$^{31}$P NMR (121 MHz, CDCl$_3$): δ/ppm=48.21 (d, J=202.2 Hz, major isomer), 46.71 (d, J=196.7 Hz, minor isomer).

Synthesis of rac-($\eta^5$:$\eta^1$-Indenyl-CH(Cy) CH$_2$CH$_2$SMe)Ru$^{11}$(PPh$_3$)Cl

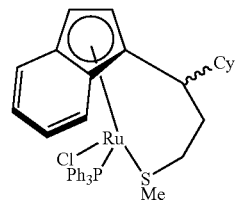

A solution of ligand rac-3-(1-cyclohexyl-3-methansulfanyl-propyl)-1H-indene (72 mg, 0.25 mmol) in toluene (8 mL) was cooled to −78° C. and n-BuLi (2.5 M solution in hexanes, 0.11 mL, 0.28 mmol) added dropwise, in the dark. The reaction was then stirred at −78° C. for 15 minutes and room temperature for 2 hours. The resulting yellow solution was transferred slowly (ca. 10 minutes) via syringe, to a suspension of dichlorotris(triphenylphosphine)ruthenium (II) (288 mg, 0.30 mmol) in toluene (5 mL) at −60° C. The dark mixture was stirred at −60° C. for 15 minutes, then warmed to reflux for 16 hours, then the reaction was cooled to room temperature and the solvents removed under vacuum. $^1$H NMR of the crude material indicated the expected complex had been formed as a ca. 1:1 mixture of (presumably) metal-centred diastereoisomers.

Purification of the complex was achieved by column chromatography (50% diethyl ether/toluene, neutral Al$_2$O$_3$, using degassed solvents) to give a rust-red solid (62 mg, 0.09 mmol, 36%) and 1:1 mixture of diastereoisomers.

The $^1$H NMR spectrum shows a 1:1 mixture of diastereoisomers, where two resonances can be clearly identified as belonging to separate isomers, this is indicated by using the description 'isomer A' and 'isomer B' for either resonance.

$^1$H NMR (400 MHz, C$_6$D$_6$): δ/ppm=8.01 (2H, t, J=8.7 Hz), 7.84 (2H, v.br.t, J=8.3 Hz), 7.39–7.45 (2H, m), 7.28–7.37 (1H, m), 7.20 (6H, td, J=7.5, 1.1 Hz), 7.08–7.16 (5H, m), 6.94–7.00 (1H, m), 4.89 (½H, br.s, Cp-H—isomer A), 3.67 (1½H, v.br.s, Cp-H—isomer B), 2.98 (½H, dd, J=3.9, 2.1 Hz, Cp-H—isomer A), 2.64 (½H, v.br.s, Cp-H—isomer B), 2.41 (½H, dd, J=12.3, 4.3 Hz), 2.34 (½H, dd, J=13.7, 2.9 Hz), 2.20 (½H, s, SMe—isomer A), 2.12 (1½H, s, SMe—isomer B), 1.49–1.82 (7H, m), 0.71–1.46 (8H, m).

$^{31}$P NMR (121 MHz, C$_6$D$_6$): δ/ppm=59.98 (s).

What is claimed is:

1. A compound of formula (1):

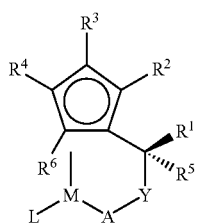

(1)

wherein:
L is optionally one or more groups which are removable during a chemical reaction;
M is a transition metal selected from Groups 6, 7, 8, 9 and 10;
Y is an optionally substituted linking group;
A is an optionally substituted heteroatom capable of bonding or coordinating to metal (M); and
EITHER:
(a) R$^5$ and R$^6$ are hydrogen:
R$^1$ is optionally substituted hydrocarbyl, optionally substituted heterocyclyl, or tri-hydrocarbylsilyl, or R$^1$ & Y are linked in such a way as to form an asymmetrically substituted ring, or R$^1$ & A are linked in such a way as to form an optionally substituted heterocyclic ring;
R$^2$ is optionally substituted hydrocarbyl, optionally substituted heterocyclyl, or tri-hydrocarbylsilyl;
R$^3$ and R$^4$ are independently optionally substituted hydrocarbyl, optionally substituted heterocyclyl, tri-hydrocarbylsilyl or hydrogen; or
one or more of R$^2$ & R$^3$ and R$^3$ & R$^4$ are linked in such a way as to form an optionally substituted ring optionally comprising one or more heteroatoms; provided that R$^2$, R$^3$ and R$^4$ are selected such that the cyclopentadiene ring to which they are attached is asymmetrically substituted;
OR;
(b) R$^3$ is hydrogen, optionally substituted hydrocarbyl, optionally substituted heterocyclyl, or tri-hydrocarbylsilyl; and either
(i) R$^5$ & R$^2$ are linked in such a way as to form an optionally substituted non-aromatic ring system optionally comprising one or more heteroatoms; and R$^1$, R$^4$ and R$^6$ are independently hydrogen, optionally substituted hydrocarbyl, optionally substituted heterocyclyl, or tri-hydrocarbylsilyl; or
R$^1$ & R$^6$ are linked in such a way as to form an optionally substituted non-aromatic ring system optionally comprising one or more heteroatoms and R$^4$ is hydrogen, optionally substituted hydrocarbyl, optionally substituted heterocyclyl, or tri-hydrocarbylsilyl; or R$^4$ & R$^6$ are linked in such a way as to form an optionally substituted ring optionally comprising one or more heteroatoms and R$^1$ is hydrogen, optionally substituted hydrocarbyl, optionally substituted heterocyclyl, or tri-hydrocarbylsilyl; or (ii) R$^5$, R$^1$ & R$^2$ are linked in such a way as to form an optionally substituted non-aromatic asymmetric ring system optionally comprising one or more heteroatoms; and R$^4$ and R$^6$ are idependently hydrogen, optionally substituted hydrocarbyl, optionally substituted heterocyclyl, or tri-hydrocarbylsilyl; or R$^4$ & R$^6$ are linked in such a way as to form an optionally substituted ring optionally comprising one or more heteroatoms.

2. A compound of formula (1);

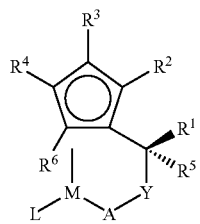

(1)

wherein:
L is, independently, one or more groups which are removable during a chemical reaction;
M is rhodium, ruthenium, iridium, cobalt, iron, manganese, chromium, tungsten, molybdenum, nickel, palladium, or platinum;
Y is a linking chain comprising an optionally substituted C$_{1-5}$ alkyl or alkylaryl, or optionally substituted silyl bridge, or optionally substituted heteroatom containing bridge;
A is an atom (which may carry substituents) which may bond to the metal; and
EITHER:
(a) R$^5$ and R$^6$ are hydrogen;
R$^1$ and R$^2$ are trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or R$^2$ is as above and R$^1$ joins to Y to form an asymmetrically substituted C$_{3-8}$ cycloalkyl, C$_{3-8}$ cycloalkenyl or C$_{3-8}$ heterocyclyl ring optionally substituted with hydroxy, trialkylsilyl, alkyl, alkoxy, aryl, arylalkyl, aryloxyallyl, alkoxyalkyl, alkoxyalkoxyalkyl, cycloalky, cycloalkylalkyl, heteroaryl, heteroarylalkyl or heteroaryloxyalkyl; or R$^2$ is as above and R$^1$ joins to A to form an optionally substituted heterocyclic ring; R$^3$ and R$^4$ are the same or different and are selected from the substituents already recited for R$^1$ and R$^2$ and may also be, independently, hydrogen; or, one or more of R$^2$ and R$^3$, R$^3$ and R$^4$ join to form an optionally substituted ring optionally comprising one or more heteroatoms OR:
(b) R$^3$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; and either (I) $R^5$ and $R^2$ join to form an optionally substituted non-aromatic ring system optionally comprising one or more heteroatoms; and $R^1$, $R^4$ and $R^5$ are independently hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ & $R^6$ join to form an optionally substituted non-aromatic ring system optionally comprising one or more heteroatoms and $R^4$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^4$ & $R^6$ join to form an optionally substituted ring system optionally comprising one or more heteroatoms and $R^1$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or (ii) $R^5$, $R^1$ and $R^2$ are linked in such a way as to form an optionally substituted non-aromatic asymmetric ring system comprising one or more heteroatoms; and $R^4$ and $R^6$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^4$ & $R^6$ join to form an optionally substituted ring system optionally comprising one or more heteroatoms.

3. A compound of Formula (2) or (3):

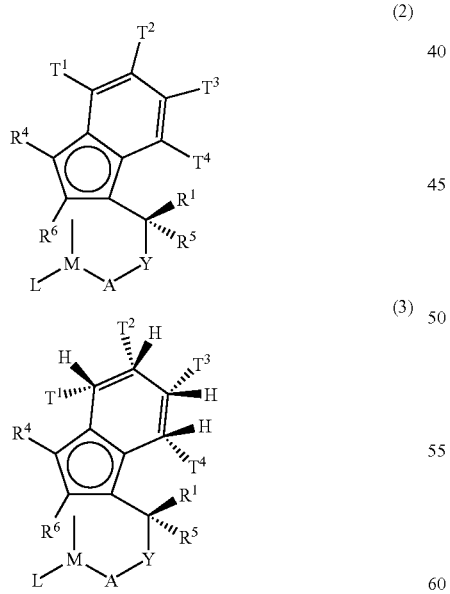

wherein:

L are independently one or more groups which are removable during a chemical reaction;

M is rhodium, ruthenium, iridium, cobalt, iron, manganese, chromium, tungsten, molybdenum, nickel, palladium, or platinum;

Y is a linking chain comprising an optionally substituted $C_{1-5}$alkyl or alkylaryl, or optionally substituted silyl bridge, or optionally substituted hetereoatom containing bridge;

A is an atom (which may carry substituents) which may bond to the metal;

$R^1$ is trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ joins to Y to form an asymmetrically substituted $C_{3-8}$cycloalkyl, $C_{3-8}$cycloalkenyl or $C_{3-8}$heterocyclyl ring optionally substituted with hydroxy, trialkylsilyl, alkyl, alkoxy, aryl, arylalkyl, aryloxyallyl, alkoxyalkyl, alkoxyalkoxyalkyl, cycloalky, cycloalkylalkyl, heteroaryl, heteroarylalkyl or heteroaryloxyalkyl; or $R^1$ joins to A to form an optionally substituted heterocyclic ring;

$R^4$ is hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl;

$R^6$ is hydrogen; and $T^1$, $T^2$, $T^3$, $T^4$ are the same or different and are hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl.

4. A compound according to claim 3 wherein:

Y is $(CH_2)_n$, where n is 1, 2, or 3;

M—L is Rh(CO) or Ru(PPh$_3$)Cl;

$T^{1-4}$ are independently hydrogen or alkyl;

$R^1$ is alkyl, aryl, cycloalkyl; and $R^4$ is hydrogen, alkyl, aryl, cycloalkyl or trialkylsilyl.

5. A compound according to claim 3 wherein:

Y is $CR^{10}R^1$

M—L is Rh(CO) or RU(PPh$_3$)Cl;

$T^{1-4}$ are hydrogen;

$R^1$ is alkyl, aryl, cycloalkyl;

$R^4$ is hydrogen; and one of $R^1$ and $R^{11}$ is hydrogen the other being napthyl or phenyl.

6. A compound of formula (4) or (5):

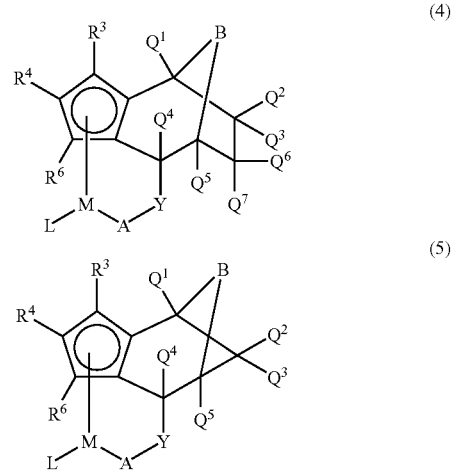

wherein:

L is independently one or more groups which are removable during a chemical reaction;

M is rhodium, ruthenium, iridium, cobalt, iron, manganese, chromium, tungsten, molybdenum, nickel, palladium, or platinum, Y is a linking chain comprising an optionally substituted $C_{1-5}$alkyl or alkylaryl, or optionally substituted silyl bridge, or optionally substituted hetereoatom containing bridge;

A is an atom (which may carry substituents) which may bond to the metal;

B is a bridge comprising an optionally substituted $C_{1-3}$alkyl bridge or an optionally substituted 1–3 atom bridge wherein at least one atom is a heteroatom and any remaining atoms are carbon atoms, preferably wherein any heteroatoms are selected from the group comprising N, O, P, S and Si;

Y is an optionally substituted $C_{1-3}$alkyl bridge; and $R^3$, $R^4$, $R^6$, $R^8$, $R^9$, $Q^1$, $Q^2$, $Q^3$, $Q^4$, $Q^5$, $Q^6$, $Q^7$ are the same or different and are hydrogen, trialkylsilyl, dialkylarylsilyl, alkyldiarylsilyl, triarylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^4$ & $R^6$ are linked in such a way as to form an optionally substituted ring optionally comprising one or more heteroatoms; or $Q^4$ & $R^6$ are linked in such a way as to form an optionally substituted non-aromatic ring system comprising one or more heteratoms; and additionally $Q^2$ and $Q^3$ may also be alkoxy, aryloxy or silyloxy; or $Q^2$ and $Q^3$ combine to form a carbonyl, imine, or alkylidene group.

7. A compound according to claim 6 wherein the compound is a compound of formula (8) and (9):

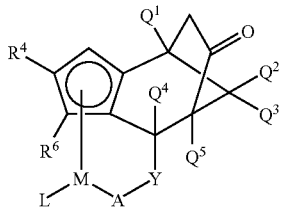

(8)

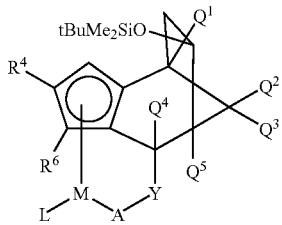

(9)

wherein:
M—L is Rh(CO) or Ru(PPh$_3$)Cl;
Y is $(CH_2)_n$ where n=1, 2 or 3;
$Q^3$ & $Q^5$ are each H;
A is PPh$_2$;
$Q^1$ is hydrogen or alkyl;
$Q^2$ is hydrogen, alkyl, aryl or cycloalkyl; and
EITHER
$Q^4$ is hydrogen, alkyl or aryl; and
$R^4$ and $R^6$ are each hydrogen or $R^4$ & $R^6$ are —(CH$_2$)$_4$—;
OR
$R^4$ is hydrogen; and
$Q^4$ & $R^6$ are —(CH$_2$)$_3$—.

8. A compound according to claim 6 wherein the compound is a compound of formula (10) and (11):

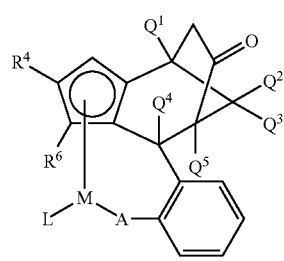

(10)

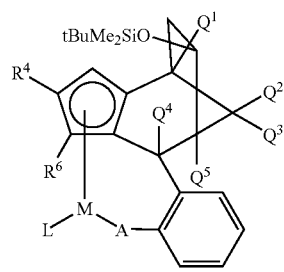

(11)

wherein:
M—L=Rh(CO) or Ru(PPh$_3$)Cl;
$Q^3$ & $Q^5$ are each H;
A is PPh$_2$;
$Q^1$ is hydrogen or alkyl;
$Q_2$ is hydrogen, alkyl, aryl or cycloalkyl; and
EITHER
$Q^4$ is hydrogen, alkyl or aryl; and
$R^4$ and $R^6$ are each hydrogen or $R^4$ & $R^6$ are —(CH$_2$)$_4$—;
OR
$R^4$ is hydrogen; and
$Q^4$ & $R^6$ are —(CH$_2$)$_3$—.

9. A compound according to claim 6 wherein the compound is a compound of formula (12) and (13):

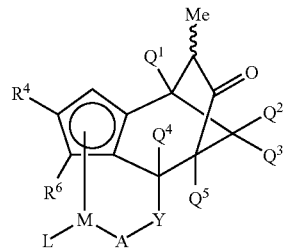

(12)

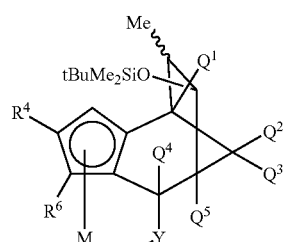

(13)

wherein:
M—L is Rh(CO) or Ru(PPh$_3$)Cl;

Y is $(CH_2)_n$, where n=1, 2 or 3;
$Q^1$, $Q^3$ & $Q^5$ are each H;
A is $PPh_2$;
$Q^2$ is $CHMe_2$ or $C(Me)=CH_2$; and
EITHER
$Q^4$ is hydrogen, alkyl or aryl; and
$R^4$ and $R^5$ are each hydrogen or $R^4$ & $R^6$ are —$(CH_2)_4$—;
OR
$R^4$ is hydrogen; and
$Q^4$ & $R^6$ are —$(CH_2)_3$—.

10. A compound according to claim 6 wherein the compound is a compound of formula (14) and (15):

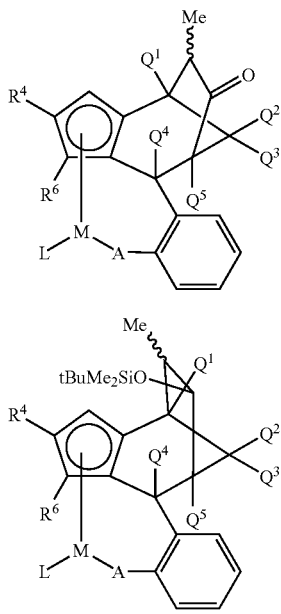

wherein:
M—L is Rh(CO) or Ru(PPh_3)Cl;
$Q^1$, $Q^3$ & $Q^5$ are each H;
A is $PPh_2$;
$Q^2$ is $CHMe_2$ or $C(Me)=CH_2$; and
EITHER
$Q^4$ is hydrogen, alkyl or aryl; and
$R^4$ and $R^5$ are each hydrogen or $R^4$ & $R^6$ are —$(CH_2)_4$—;
OR
$R^4$ is hydrogen; and
$Q^4$ & $R^6$ are —$(CH_2)_3$—.

11. A compound according to any one of claims 1, 2, 3 or 6 wherein M is rhodium, iridium or ruthenium.

12. In a catalytic asymmetric synthesis for producing a chiral product, the improvement wherein the catalyst is a compound according to any one of claims 1, 2, 3 or 6.

13. A compound according to claim 2 wherein A is $PR^8R^9$, $NR^8$, $NR^8R^9$ O, $OR^8$, S or $SR^8$ wherein $R^8$ and $R^9$ may be independently hydrogen, alkyl, aryl, arylalkyl, aryloxyalkyl, alkoxyalkyl, alkoxyalkoxyalkyl, cycloalkyl, cycloalkylalkyl, heteroaryl, heteroarylalkyl, heteroaryloxyalkyl, trialkylsilyl, dialkylarylsilyl, alkyldiarylsilyl, triarylsilyl, acyl, arylsulphonate or alkylsulphonate.

14. A compound according to claim 3 wherein A is $PR^8R^9$, $NR^8$, $NR^8R^9$ or $SR^8$ wherein $R^8$ and $R^9$ may be independently hydrogen, alkyl, aryl, arylalkyl, aryloxyalkyl, alkoxyalkyl, alkoxyalkoxyalkyl, cycloalkyl, cycloalkylalkyl, heteroaryl, heteroarylalkyl, heteroaryloxyalkyl, trialkylsilyl, dialkylarylsilyl, alkyldiarylsilyl, triarylsilyl, acyl, arylsulphonate or alkylsulphonate.

15. A compound according to claim 6 wherein A is $PR^8R^9$, $NR^8_3$, $NR^8R^9$ or $SR^8$ wherein $R^8$ and $R^9$ may be independently hydrogen, alkyl, aryl, arylalkyl, aryloxyalkyl, alkoxyalkyl, alkoxyalkoxyalkyl, cycloalkyl, cycloalkylalkyl, heteroaryl, heteroarylalkyl, heteroaryloxyalkyl, trialkylsilyl, dialkylarylsilyl, alkyldiarylsilyl, triarylsilyl, acyl, arylsulphonate or alkylsulphonate.

* * * * *